US010953043B2

(12) United States Patent
Tarbet et al.

(10) Patent No.: US 10,953,043 B2
(45) Date of Patent: Mar. 23, 2021

(54) NANOPARTICLE COMPOSITIONS AND METHODS FOR TREATING OR PREVENTING TISSUE INFECTIONS AND DISEASES

(71) Applicant: ATTOSTAT, INC., North Salt Lake, UT (US)

(72) Inventors: Bryon J. Tarbet, Highland, UT (US); William H. Niedermeyer, West Jordan, UT (US)

(73) Assignee: ATTOSTAT, INC., North Salt Lake, UT (US)

( * ) Notice: Subject to any disclaimer, the term of this patent is extended or adjusted under 35 U.S.C. 154(b) by 0 days.

(21) Appl. No.: 15/825,912

(22) Filed: Nov. 29, 2017

(65) Prior Publication Data

US 2018/0078580 A1 Mar. 22, 2018

Related U.S. Application Data

(62) Division of application No. 15/088,863, filed on Apr. 1, 2016, now Pat. No. 9,839,652.

(Continued)

(51) Int. Cl.
*A61K 9/06* (2006.01)
*A61K 33/24* (2019.01)
(Continued)

(52) U.S. Cl.
CPC ............ *A61K 33/38* (2013.01); *A61K 9/0014* (2013.01); *A61K 9/0019* (2013.01);
(Continued)

(58) Field of Classification Search
CPC .... A61K 2300/00; A61K 33/24; A61K 33/38; A61K 36/00; A61K 47/46; A61K 9/0014;
(Continued)

(56) References Cited

U.S. PATENT DOCUMENTS 3,133,023 A 5/1964 Vogel
4,121,017 A 10/1978 Dougherty et al.
(Continued)

FOREIGN PATENT DOCUMENTS

CA 2560837 3/2007
CN 101128550 2/2008
(Continued)

OTHER PUBLICATIONS

Samberg et al. (Nanotoxicology 2011;5(2):244-253) (Year: 2011).*
(Continued)

*Primary Examiner* — Ernst V Arnold
(74) *Attorney, Agent, or Firm* — Workman Nydegger

(57) ABSTRACT

Stabilized multi-component antimicrobial compositions for treating tissue diseases, infections or conditions include a first and second set of differently sized and/or differently shaped metal nanoparticles, and a stabilizing agent. Compositions and treatment methods may be used for treating tissue diseases, infections or conditions caused by microbial infections, such as bacteria, viral, and/or fungal infections, or for preventing the infection of a wound, such as a cut, abrasion, ulcer, lesion, sore, and the like. The compositions and treatment methods disclosed herein may also be used as a prophylactic, and in some embodiments may be applied to otherwise healthy tissue in order to prevent or reduce the occurrence of a tissue disease, infection or condition.

21 Claims, 6 Drawing Sheets

Related U.S. Application Data

(60) Provisional application No. 62/141,692, filed on Apr. 1, 2015, provisional application No. 62/168,094, filed on May 29, 2015.

(51) Int. Cl.

| | | |
|---|---|---|
| *A61L 31/16* | (2006.01) | |
| *A61K 33/38* | (2006.01) | |
| *A61L 27/30* | (2006.01) | |
| *A61K 9/00* | (2006.01) | |
| *A61K 9/08* | (2006.01) | |
| *A61K 9/107* | (2006.01) | |
| *A61K 47/46* | (2006.01) | |
| *A61K 9/16* | (2006.01) | |
| *A61L 29/10* | (2006.01) | |
| *A61L 29/16* | (2006.01) | |
| *A61L 31/08* | (2006.01) | |
| *A61K 36/00* | (2006.01) | |

(52) U.S. Cl.
CPC .......... *A61K 9/0043* (2013.01); *A61K 9/0073* (2013.01); *A61K 9/06* (2013.01); *A61K 9/08* (2013.01); *A61K 9/107* (2013.01); *A61K 9/1664* (2013.01); *A61K 33/24* (2013.01); *A61K 47/46* (2013.01); *A61L 27/306* (2013.01); *A61L 29/106* (2013.01); *A61L 29/16* (2013.01); *A61L 31/088* (2013.01); *A61L 31/16* (2013.01); *A61K 36/00* (2013.01); *A61L 2400/06* (2013.01); *A61L 2400/12* (2013.01); *A61L 2420/06* (2013.01)

(58) Field of Classification Search
CPC .. A61K 9/0019; A61K 9/0043; A61K 9/0073; A61K 9/06; A61K 9/08; A61K 9/107; A61K 9/1664; A61L 2400/06; A61L 2400/12; A61L 2420/06; A61L 27/306; A61L 29/106; A61L 29/16; A61L 31/088; A61L 31/16
See application file for complete search history.

(56) References Cited

U.S. PATENT DOCUMENTS

| | | | |
|---|---|---|---|
| 4,515,740 | A | 5/1985 | Schuttenberg et al. |
| 5,047,448 | A | 9/1991 | Tanaka |
| 5,227,608 | A | 7/1993 | Yoshida |
| 5,390,864 | A | 2/1995 | Alexander |
| 5,585,020 | A | 12/1996 | Becker et al. |
| 5,677,075 | A | 10/1997 | Fujita |
| 6,051,279 | A | 4/2000 | Gualco et al. |
| 6,232,264 | B1 | 5/2001 | Lukehart |
| 6,239,453 | B1 | 5/2001 | Yamada et al. |
| 6,509,070 | B1 | 1/2003 | Voevodin et al. |
| 6,660,379 | B1 | 12/2003 | Lakowicz |
| 6,720,006 | B2 | 4/2004 | Hanke |
| 7,014,737 | B2 | 3/2006 | Harutyunyan et al. |
| 7,252,814 | B2 | 8/2007 | De Mello |
| 7,332,351 | B2 | 2/2008 | Tan et al. |
| 7,371,457 | B2 | 5/2008 | Oldenburg et al. |
| 7,374,730 | B2 | 5/2008 | Simard et al. |
| 7,384,560 | B2 | 6/2008 | Martens et al. |
| 7,449,679 | B2 | 11/2008 | Plewa |
| 7,509,993 | B1 | 3/2009 | Turng et al. |
| 7,527,824 | B2 | 3/2009 | Becker |
| 7,553,801 | B2 | 6/2009 | Alexander et al. |
| 7,625,637 | B2 | 12/2009 | Kim |
| 7,662,731 | B2 | 2/2010 | Itoh et al. |
| 7,682,970 | B2 | 3/2010 | Grigoropoulos et al. |
| 7,700,032 | B1 | 4/2010 | Lu et al. |
| 7,884,160 | B2 | 2/2011 | Wang et al. |
| 7,967,876 | B2 | 6/2011 | Aradi |
| 7,985,367 | B2 | 7/2011 | Hiromatsu et al. |
| 8,097,233 | B2 | 1/2012 | Porterat |
| 8,435,602 | B1 | 5/2013 | Seal |
| 8,490,583 | B1 | 7/2013 | Gardenier |
| 8,490,586 | B2 | 7/2013 | Gardenier |
| 8,524,139 | B2 | 9/2013 | Toth |
| 8,685,293 | B1 | 4/2014 | Coppa et al. |
| 8,709,531 | B2 | 4/2014 | Miller |
| 8,802,234 | B2 | 8/2014 | Che |
| 8,883,865 | B2 | 11/2014 | DiFrancesco |
| 8,992,815 | B2 | 3/2015 | Hu |
| 9,259,407 | B2 | 2/2016 | Baker et al. |
| 9,434,006 | B2 | 9/2016 | Niedermyer |
| 9,463,510 | B2 | 10/2016 | Hendi et al. |
| 9,512,377 | B2 | 12/2016 | Binder |
| 9,627,713 | B2 | 4/2017 | Moganty et al. |
| 9,839,652 | B2 | 12/2017 | Tarbet et al. |
| 9,849,512 | B2 | 12/2017 | Niedermeyer |
| 9,883,670 | B2 | 2/2018 | Niedermeyer |
| 9,885,001 | B2 | 2/2018 | Niedermeyer |
| 10,099,191 | B1 | 10/2018 | Lu et al. |
| 2001/0031564 | A1 | 10/2001 | Suzuki et al. |
| 2002/0051823 | A1 | 5/2002 | Yan |
| 2003/0012686 | A1 | 1/2003 | Andersen et al. |
| 2003/0086859 | A1 | 5/2003 | Kawakami et al. |
| 2003/0102099 | A1 | 6/2003 | Yadav et al. |
| 2003/0108612 | A1 | 6/2003 | Xu |
| 2003/0129320 | A1 | 7/2003 | Yu |
| 2003/0228525 | A1 | 12/2003 | Kozawa |
| 2004/0103936 | A1 | 6/2004 | Andriessen |
| 2004/0214001 | A1 | 10/2004 | Oldenburg et al. |
| 2005/0061779 | A1 | 3/2005 | Blumenfeld |
| 2005/0061785 | A1 | 3/2005 | Schroder |
| 2005/0153071 | A1 | 7/2005 | Bouvrette |
| 2005/0158506 | A1 | 7/2005 | Waki et al. |
| 2005/0247866 | A1 | 11/2005 | Plewa et al. |
| 2005/0258149 | A1 | 11/2005 | Glukhoy |
| 2005/0260276 | A1 | 11/2005 | Yang et al. |
| 2006/0049034 | A1 | 3/2006 | Lee |
| 2006/0142853 | A1 | 6/2006 | Wang et al. |
| 2007/0003603 | A1 | 1/2007 | Karandikar |
| 2007/0029185 | A1 | 2/2007 | Tung |
| 2007/0125196 | A1 | 6/2007 | Zhong et al. |
| 2007/0140951 | A1 | 6/2007 | O'Brien |
| 2007/0141259 | A1 | 6/2007 | House et al. |
| 2007/0207335 | A1 | 9/2007 | Karandikar |
| 2007/0269576 | A1 | 11/2007 | Barton et al. |
| 2007/0287202 | A1 | 12/2007 | Maehashi et al. |
| 2008/0006524 | A1 | 1/2008 | Liu |
| 2008/0035682 | A1 | 2/2008 | Coffey et al. |
| 2008/0044148 | A1 | 2/2008 | Robinson |
| 2008/0050448 | A1 | 2/2008 | Wilson |
| 2008/0143021 | A1 | 6/2008 | Ehrentraut |
| 2008/0161631 | A1 | 7/2008 | Axtell et al. |
| 2008/0241490 | A1 | 10/2008 | Newman et al. |
| 2008/0263940 | A1 | 10/2008 | Parish et al. |
| 2008/0292673 | A1 | 11/2008 | Crudden |
| 2009/0000186 | A1 | 1/2009 | Sanders et al. |
| 2009/0028947 | A1 | 1/2009 | Rahman |
| 2009/0039316 | A1 | 2/2009 | Hirai |
| 2009/0061230 | A1 | 3/2009 | Berkei |
| 2009/0104179 | A1 | 4/2009 | Boyden |
| 2009/0117268 | A1 | 5/2009 | Lewis et al. |
| 2009/0148484 | A1 | 6/2009 | Lin et al. |
| 2009/0175948 | A1* | 7/2009 | Jiang ............... A01N 59/16 424/490 |
| 2009/0191288 | A1 | 7/2009 | Squires |
| 2009/0246530 | A1 | 10/2009 | Murakami et al. |
| 2010/0040655 | A1 | 2/2010 | Ren et al. |
| 2010/0050872 | A1 | 3/2010 | Lee |
| 2010/0068299 | A1 | 3/2010 | van der Krieken et al. |
| 2010/0072645 | A1 | 3/2010 | Hiromatsu et al. |
| 2010/0080957 | A1 | 4/2010 | Chinn |
| 2010/0092367 | A1 | 4/2010 | Porterat |
| 2010/0154591 | A1 | 6/2010 | Islam |
| 2010/0167958 | A1 | 7/2010 | Lin |
| 2010/0172997 | A1 | 7/2010 | Omary |
| 2010/0180413 | A1 | 7/2010 | Jeong |
| 2010/0183739 | A1 | 7/2010 | Newman |

(56) References Cited

U.S. PATENT DOCUMENTS

| | | |
|---|---|---|
| 2010/0187091 A1 | 7/2010 | Pierce et al. |
| 2010/0196192 A1 | 8/2010 | Liu et al. |
| 2010/0212221 A1 | 8/2010 | Aradi |
| 2010/0255110 A1 | 10/2010 | Yoon |
| 2010/0272650 A1 | 10/2010 | Tsukada |
| 2010/0272770 A1 | 10/2010 | De Windt |
| 2010/0301013 A1 | 12/2010 | Conneely |
| 2011/0039078 A1 | 2/2011 | Brennan Fournet et al. |
| 2011/0052460 A1 | 3/2011 | Coffey et al. |
| 2011/0129536 A1* | 6/2011 | Donati .............. C08L 5/08 424/488 |
| 2011/0155643 A1 | 6/2011 | Tov |
| 2011/0192450 A1 | 8/2011 | Liu |
| 2011/0193025 A1 | 8/2011 | Ichikawa et al. |
| 2011/0196044 A1 | 8/2011 | Hu |
| 2011/0197369 A1 | 8/2011 | Hinestroza et al. |
| 2011/0201527 A1 | 8/2011 | Lin |
| 2011/0206753 A1 | 8/2011 | Karpov |
| 2011/0228890 A1 | 9/2011 | Dean et al. |
| 2011/0244056 A1 | 10/2011 | Santra |
| 2011/0297653 A1 | 12/2011 | Ehrentraut |
| 2012/0088066 A1 | 4/2012 | Aytug et al. |
| 2012/0094036 A1 | 4/2012 | Droege et al. |
| 2012/0124899 A1 | 5/2012 | Difrancesco |
| 2012/0136164 A1 | 5/2012 | Ying et al. |
| 2012/0138347 A1 | 6/2012 | Bahnmuller |
| 2012/0138862 A1 | 6/2012 | Hogan |
| 2012/0164073 A1 | 6/2012 | Xu et al. |
| 2012/0174472 A1 | 7/2012 | Mills |
| 2012/0183674 A1 | 7/2012 | Bonn-Savage |
| 2012/0301528 A1 | 11/2012 | Uhlmann |
| 2012/0301531 A1 | 11/2012 | Uhlmann et al. |
| 2012/0313200 A1 | 12/2012 | Jackrel et al. |
| 2012/0328701 A1 | 12/2012 | Edelson |
| 2013/0001833 A1* | 1/2013 | Niedermeyer ......... B82Y 40/00 264/400 |
| 2013/0078510 A1 | 3/2013 | Reynolds et al. |
| 2013/0116369 A1 | 5/2013 | Qi et al. |
| 2013/0152823 A1 | 6/2013 | El-Sayed |
| 2013/0203849 A1 | 8/2013 | Ben Yehuda |
| 2013/0224477 A1 | 8/2013 | Xu |
| 2013/0273116 A1 | 10/2013 | Jespersen et al. |
| 2013/0334104 A1 | 12/2013 | Halas |
| 2013/0337998 A1 | 12/2013 | Irving |
| 2014/0024026 A1 | 1/2014 | Alocilja |
| 2014/0178513 A1 | 6/2014 | Matthews |
| 2014/0221543 A1 | 8/2014 | Wang |
| 2014/0274830 A1 | 9/2014 | Pol et al. |
| 2014/0288194 A1 | 9/2014 | Niedermeyer |
| 2014/0322351 A1* | 10/2014 | Gawande ............. A01N 59/12 424/618 |
| 2014/0370293 A1 | 12/2014 | Johnson |
| 2015/0008313 A1 | 1/2015 | Loboda |
| 2015/0030919 A1 | 1/2015 | Koazawa |
| 2015/0066135 A1 | 3/2015 | Weber et al. |
| 2015/0190550 A1 | 7/2015 | Nusko et al. |
| 2016/0081346 A1 | 3/2016 | Niedermeyer |
| 2016/0082514 A1 | 3/2016 | Niedermeyer |
| 2016/0083146 A1 | 3/2016 | Niedermeyer |
| 2016/0083901 A1 | 3/2016 | Niedermeyer |
| 2016/0144350 A1 | 5/2016 | Aizenberg et al. |
| 2016/0298243 A1 | 10/2016 | Tarbet et al. |
| 2016/0372243 A1 | 12/2016 | Cassignol |
| 2017/0129975 A1 | 5/2017 | Hallinan et al. |
| 2017/0136112 A1 | 5/2017 | Pillich et al. |
| 2017/0166485 A1 | 6/2017 | Hong et al. |
| 2017/0209490 A1 | 7/2017 | Niedermeyer |
| 2018/0078580 A1 | 3/2018 | Tarbet et al. |
| 2018/0126463 A1 | 5/2018 | Niedermeyer |
| 2018/0282852 A1 | 10/2018 | Soloway |
| 2019/0225498 A1 | 7/2019 | Ruiz et al. |

FOREIGN PATENT DOCUMENTS

| | | |
|---|---|---|
| CN | 101415644 | 4/2009 |
| CN | 101716684 | 6/2010 |
| CN | 101932752 | 12/2010 |
| CN | 101960070 | 1/2011 |
| CN | 102120619 | 7/2011 |
| CN | 101180372 | 5/2012 |
| CN | 102753628 | 10/2012 |
| CN | 103796946 | 5/2014 |
| CN | 103891558 | 7/2014 |
| CN | 104014811 | 9/2014 |
| DE | 102005044360 | 3/2007 |
| EP | 2140958 | 1/2010 |
| EP | 2559436 | 2/2013 |
| JP | 2008527169 | 7/2008 |
| JP | 2010001528 | 1/2010 |
| KR | 20060021749 | 3/2006 |
| WO | 2006026026 | 3/2006 |
| WO | 2006053225 | 5/2006 |
| WO | 2006062826 | 6/2006 |
| WO | 2006/126823 A1 | 11/2006 |
| WO | 2008043396 | 4/2008 |
| WO | 2008153239 | 12/2008 |
| WO | 2009025955 | 2/2009 |
| WO | 2009044146 | 4/2009 |
| WO | 2009046081 | 4/2009 |
| WO | 2009066011 | 5/2009 |
| WO | 2009091900 | 7/2009 |
| WO | 2011045627 | 4/2011 |
| WO | 2012082364 | 6/2012 |
| WO | 2013006430 | 1/2013 |
| WO | WO2013141879 | 9/2013 |
| WO | WO2014066850 | 5/2014 |
| WO | 2014096556 | 6/2014 |
| WO | 2014137352 | 9/2014 |
| WO | 2014/190097 A1 | 11/2014 |
| WO | WO2016007113 | 1/2015 |
| WO | WO2016007112 | 1/2016 |

OTHER PUBLICATIONS

Prabhu et al. (International Nano Letters 2012;2(32):10 pages). (Year: 2012).*

Pal et al. (Applied and Environmental Microbiology 2007;73(6):1712-1720) (Year: 2007).*

Gogoi et al. (Langmuir 2006;22:9322-9328) (Year: 2006).*

U.S. Appl. No. 15/808,088, filed Nov. 9, 2017, Niedermeyer.

Badawy et al., "Surface Charge-Dependent Toxicity of Silver Nanoparticles", Environ. Sci. Technol. 2011, 45, 283-287.

Barcikowski et al., "Generation of nanoparticle colloids by picosecond and femtosecond laser ablations in liquid flow", Appl. Phys. Lett. 91, 083113 (2007).

Chien et al., "Synthesis of nanoparticles: sunlight formation of gold nanodecahedra for ultra-sensitive lead-ion detection", Green Chem., vol. 13, pp. 1162-1166, May 2011.

Hultin, "A Guide to Solvents and Reagents in Introductory Organic Chemistry for students in 2.222", Obtained from https://home.cc.umanitoba.ca/-hultin/chem2220/Support/solvents_and_reagents.pdf on Jan. 25, 2018, originally published Feb. 12, 2002—17 pages.

International Search Report for PCT App. No. PCT/US2012/044907 dated Jan. 13, 2013.

International Search Report for PCT App. No. PCT/US2015/051642 dated Dec. 14, 2015.

International Search Report for PCT App. No. PCT/US2015/051639 dated Dec. 17, 2015.

International Search Report for PCT App. No. PCT/US2015/051640 dated Dec. 17, 2015.

International Search Report for PCT App. No. PCT/US2015/051643 dated Dec. 17, 2015.

International Search Report for PCT App. No. PCT/US2015/051649 dated Dec. 17, 2015.

International Search Report for PCT App. No. PCT/US2015/051646 dated Dec. 18, 2015.

(56) References Cited

OTHER PUBLICATIONS

Jacobson, "These six diseases should worry you more than Ebola", Inside Energy Oct. 2014; [online] retrieved on Jan. 29, 2017 from http://www.pbs.org/newshour/updates/six-diseases-actually-worry/; 10 pages.
Jana et al., "Seeding Growth for Size Control of 5-40 nm Diameter Gold Nanoparticles", Langmuir 2001, 17, 6782-6786.
Liu et al., "A novel coral-like porous SnO2 hollow architecture: biomimetic swallowing growth mechanism and enhanced photovoltaic property for dye-sensitized solar cell application", Chem. Commun., vol. 46, pp. 472-474, 2010.
Mafuné et al., "Formation of Stable Platinum Nanoparticles by Laser Ablation in Water", J. Phys. Chem. B 2003, 107, 4218-4223.
Mycozil, "The Benefits of Colloidal Silver for Toenail Fungus", http://www.nailfungustoenail.com/benefitsofcolloidalsilverfortoenailfungus.html.
Pal et al., "Does the Antibacterial Activity of Silver Nanoparticles Depend on the Shape of the Nanoparticle?", Applied and Environmental Microbiology, 2007; 73(6): 1712-1720.
Phuoc et al, "Synthesis of Ag-deoionized water nanofluids using multi-beam laser ablation in fluids", Optics and Lasers in Engineering 45 (2007) 1099-1106.
Prabhu et al., "Silver nanoparticles: mechanism of antimicrobial action, synthesis, medical applications, and toxicity effects", International Nano Letters, 2012, 2:32, pp. 1-10.
Rawashdeh et al., "Antibacterial Mechanisms of Metallic Nanoparticles: A Review", Dynamic Biochemistry, Process Biotechnology and Molecular Biology 2009 pp. 12-20.
Riabinina et al., "Influence of pressure on the Pt nanoparticle growth modes during pulsed laser ablation", Journal of Applied Physics 108, 034322 (2010, published online Aug. 12, 2010).
Sahu et al., "Flower Shaped Silver Nanostructures: An Efficient Bacteria Exterminator", A Search for Antibacterial Agents; Chapter 2; [online] retrieved from: http://www.intechopen.com/books/a-search-for-antibacterial-agents; 2007; 73(6): 1712-1720.
Santos et al., "Enhancemetn of antibiotic effect via gold:silver-alloy nanoparticles", J. Nanopart Res (2012) 14:859, pp. 1-8.
Sylvestre et al., "Surface Chemistry of Gold Nanoparticles Produced by Laser Ablation in Aqueous Media", J Phys. Chem. B 2004, 108, 16864-16869.
Sweeney et al., "Rapid Purification and Size Separation of Gold Nanoparticles via Diafiltration", J. Am. Chem. Soc. 2006, 128, 3190-3197 (Published on web Feb. 18, 2006).
Theodorou et al., "Inhalation of Silver Nanomaterials—Seeing the Risks", International Journal of Molecular Sciences, 2014, 15, 23936-23974.
U.S. Appl. No. 13/175,708, filed Jul. 1, 2011 Office Action dated May 30, 2014.
U.S. Appl. No. 13/175,708, filed Jul. 1, 2011 Final Office Action dated Nov. 13, 2014.
U.S. Appl. No. 13/175,708, filed Jul. 1, 2011 Office Action dated Jul. 6, 2015.
U.S. Appl. No. 14/861,243, filed Sep. 22, 2015 Office Action dated Mar. 9, 2016.
U.S. Appl. No. 13/175,708, filed Jul. 1, 2011 Final Office Action dated Mar. 28, 2016.
U.S. Appl. No. 14/861,318, filed Sep. 22, 2015 Office Action dated Apr. 25, 2016.
U.S. Appl. No. 14/861,318, filed Sep. 22, 2015 Notice of Allowance dated May 20, 2016.
U.S. Appl. No. 14/861,318, filed Sep. 22, 2015 Corrected Notice of Allowance dated Jun. 15, 2016.
U.S. Appl. No. 14/861,243, filed Sep. 22, 2015 Final Office Action dated Jul. 26, 2016.
U.S. Appl. No. 14/861,442, filed Sep. 22, 2015 Office Action dated Sep. 29, 2016.
U.S. Appl. No. 14/861,243, filed Sep. 22, 2015 Office Action dated Nov. 2, 2016.
U.S. Appl. No. 14/861,562, filed Sep. 22, 2015 Office Action dated Dec. 7, 2016.
U.S. Appl. No. 14/861,243, filed Sep. 22, 2015 Final Office Action dated Jan. 27, 2017.
U.S. Appl. No. 15/088,863, filed Apr. 1, 2016 Office Action dated Feb. 3, 2017.
U.S. Appl. No. 13/175,708, filed Jul. 1, 2011 Office Action dated Feb. 10, 2017.
U.S. Appl. No. 14/861,442, filed Sep. 22, 2015 Final Office Action dated Feb. 22, 2017.
U.S. Appl. No. 14/298,594, filed Jun. 6, 2014 Office Action dated Mar. 21, 2017.
U.S. Appl. No. 15/415,562, filed Jan. 25, 2017 Office Action dated May 23, 2017.
U.S. Appl. No. 14/861,562, filed Sep. 22, 2015 Final Office Action dated Jun. 23, 2017.
U.S. Appl. No. 15/088,863, filed Apr. 1, 2016 Final Office Action dated Jul. 11, 2017.
U.S. Appl. No. 14/861,442, filed Sep. 22, 2015 Office Action dated Aug. 23, 2017.
U.S. Appl. No. 15/415,562, filed Jan. 25, 2017 Office Action dated Sep. 5, 2017.
U.S. Appl. No. 14/861,375, filed Sep. 22, 2015 Office Action dated Sep. 8, 2017.
U.S. Appl. No. 14/861,500, filed Sep. 22, 2015 Office Action dated Sep. 22, 2017.
U.S. Appl. No. 14/861,243, filed Sep. 22, 2015 Office Action dated Sep. 25, 2017.
U.S. Appl. No. 14/298,594, filed Jun. 6, 2014 Final Office Action dated Oct. 17, 2017.
U.S. Appl. No. 15/415,562, filed Jan. 25, 2017 Office Action dated Jan. 31, 2018.
U.S. Appl. No. 14/861,243, filed Sep. 22, 2015 Final Office Action dated Feb. 2, 2018.
U.S. Appl. No. 14/298,594, filed Jun. 6, 2014, Niedermeyer.
U.S. Appl. No. 15/976,447, filed May 10, 2018, Niedermeyer.
U.S. Appl. No. 16/012,508, filed Jun. 19, 2018, Niedermeyer.
Malvern, "The use of the Malvern Zetasizer for the measurement of Zeta Potential", article from the Internet, http://www.malvern.co.alLaboratory/zetaintm.htm> 10 pages, printed on Feb. 12, 2002.
Malvern, "Zeta Potential Theory, Dispersion stability", article from the Internet, http://www.malvern.co.uk/Laboratory/zettheo.htm >, 3 pages, printed on Feb. 12, 2002.
NOAA Ocean Service Education, "Corals", downloaded from https://oceanservice.noaa.gov/education/kits/corals/coral03_growth.html on Sep. 5, 2017.
Leisure Pro, "Coral Identification: Types of Coral (Part 1—Hard Coral)", downloaded from http://www.leisurepro.com/blog/explorethe-blue/coral-identification-types-of-coral-part-1 on Sep. 2017.
International Coral Reef Initiative, "What are Corals", downloaded from http://www.iciforum.org/about-coral-reefs/what-are-corals on Sep. 5, 2017.
U.S. Appl. No. 14/861,375, filed Apr. 3, 2018, Office Action cited in U.S. Appl. No. 14/861375 dated Apr. 3, 2018.
Hopp Bela et al, "Production of nanostructures on bulk metal samples by laser ablation for fabrication of low-reflective surfaces", applied physics a materials science & processing, Springer Berlin Heidelberg.
Yuteng Wan et al., "Modification of coral-like SnO2 nanostructures with dense TiO2 nanoparticles for a self-cleaning gas sensor", Talanta, vol. 99, pp. 394-403.
U.S. Appl. No. 15/415,562, Jun. 20, 2018, OA.
Thanaa Majied Al-Nori, "Antibacterial activity of Silver and Gold Nanoparticles against *Streptococus, Staphylococcus aureus* and *E. coli*", A1-Mustansiriya J. Sci, Vo. 23, No. 3, 2012.
Kewal K. Jain MD, FRACS, FFPM., "The Handbook of Nanomedicine" Humana Press, 2008.
International Search Report cited in PCT/US18/62864 dated Nov. 28, 2018.
Xiang Dongxi, "Study of Silver—nanoparticles on antiviral action", Journal of Dalian Medical University, vol. 31, No. 6, 2009.
U.S. Appl. No. 16/202,078, filed Nov. 27, 2018, Niedermeyer.
Hamm et al. "Ionic conductivity enhancement of sputtered gold nanoparticle-in-ionic liquid electrolytes", J Mater Chem A, 2014; 2(3): 792-803.

(56) References Cited

OTHER PUBLICATIONS

He et al. "Ionic liquid and nanoparticle hybrid systems: Emerging applications", 2017. Advances in Colloid and Interface Science, 2017; 244: 54-70.
Nakashima et al. "Preparation of fusion materials based on ionic liquids and cationic gold nanoparticles", Polymer Journal, 2015; 47:171-176.
Choudhury et al. "A highly reversible room-temperature lithium metal battery based on crosslinked hairy nanoparticles", Nature Communications, 2015; DOI: 10.1038/ncomms10101.
Gurevitch et al. "Nanocomposites of Titanium Dioxide and Polystyrene-Poly(ethylene oxide) Block Copolymer as Solid-State Electrolytes for Lithium Metal Batteries", Journal of the Electrochemical Society, 2013; 160(9): A1611-A1617.
Korf et al. "Piperidine tethered nanoparticle-hybrid electrolyte for lithium metal batteries", J Mater. Chem., 2014; 2: 11866-11873.
Lu et al. "Ionic-Liquid-Nanoparticle Hybrid Electrolytes: Applications in Lithium Metal Batteries", Angew. Chem. Int. Ed., 2014; 53: 488-492.
Pan et al. "Hybrid Electrolytes with Controlled Network Structures for Lithium Metal Batteries", Adv. Mater., 2015; 27: 5995-6001.
Tu et al. "Nanoporous Polymer-Ceramic Composite Electrolytes for Lithium Metal Batteries", Adv. Energy Mater., 2014; 4: 1300654.
Daissy Paredes, et al., "Synthesis, characterization, and evaluation of antibacterial effect of Ag nanoparticles against *Escherichia coli* OI57:h7 and methicillin-resistant *Staphylococcus aureus* (Mrsa)", Apr. 3, 2014, International Journal of Nanomedicine, p. 1717-1729.
Guangnian Xu, et al."Progress in preparation of nano-silver", 2019, Materials Review, vol. 24, No. 11, p. 139-142.
Xinxia Yue, et al., "Preparation of silver nanoparticles by tea extracts and its application in the antibacterial finishing of cotton fabric", 2014, Shanghai Textile Science & Technology, vol. 42, No. 5, p. 45-49.
U.S. Appl. No. 15/098,071, Aug. 8, 2019, Office Action.
U.S. Appl. No. 16/012,508, Dec. 11, 2018, Office Action.
U.S. Appl. No. 16/012,508, May 31, 2019, Office Action.
Agnihotri, Shekar, et al., "Immobilized silver nanoparticles enhance contact killing and show highest efficacy: elucidation of the mechanism of bacterial action of silver," Nanoscale, 2013. published Jan. 3, 2013. (Year: 2013).
Cox (https://microbiologysociety.org/blog/rabies-virus-can-we-treat-the-untreatable.html) Jun. 25, 2019, pp. 1-4 (Year: 2019).
Muller, M. "Bacterial Silver Resistance Gained by Cooperative Interspecies Redox Behavior" Antimicrobial Agents and Chemotherapy 2018, 62 (8), 1-10 (Year: 2018).
Naftulin (https://www.sciencealert.com/a-deadly-fungus-is-spreading-across-the-world-and-we-don-t-know-how-to-stop-it) Apr. 9, 2019, pp. 1-4 (Year: 2019).
Office Action received for U.S. Appl. No. 15/415,562, dated Jun. 20, 2018.
Office Action received for U.S. Appl. No. 15/825,912, dated Jul. 15, 2019.
Rhim, J-W. et al. "Preparation and characterization of bio-nanocomposite films of agarand silver nanoparticles: Laser ablation method" Carbohydrate Polymers 103 (2014) 456-465 (Year: 2014).
U.S. Appl. filed Jun. 19, 2018, Niedermeyer., U.S. Appl. No. 16/012,508.
U.S. Appl. filed Jun. 6, 2014, Neidermeyer., U.S. Appl. No. 14/298,593.
U.S. Appl. filed Jun. 6, 2014, Neidermeyer., U.S. Appl. No. 14/298,598.
U.S. Appl. filed Nov. 29, 2017, Tarbet et al., U.S. Appl. No. 15/829,512.
U.S. Appl. filed Sep. 22, 2015, Neidermeyer., U.S. Appl. No. 14/861,243.
U.S. Appl. filed Sep. 22, 2015, Neidermeyer., U.S. Appl. No. 14/861,318.
U.S. Appl. filed Sep. 22, 2015, Neidermeyer., U.S. Appl. No. 14/861,500.
U.S. Appl. filed Sep. 22, 2015, Neidermeyer., U.S. Appl. No. 14/861,562.
U.S. Appl. No. 13/175,708, filed Aug. 21, 2017, Notice of Allowance cited in U.S. Appl. No. 13/175,708 dated Aug. 21, 2017.
U.S. Appl. No. 13/175,708, filed Sep. 12, 2017, Corrected Notice of Allowance cited in U.S. Appl. No. 13/175,708 dated Sep. 12, 2017.
U.S. Appl. No. 15/098,071, filed Apr. 13, 2016, Tarbet et al.
U.S. Application mailed on Jul. 1, 2011 by Niedermeyer, U.S. Appl. No. 13/175,708.
U.S. Application mailed on Nov. 29, 2017 by Tarbet, U.S. Appl. No. 15/825,912.
U.S. Patent Application filed on Apr. 1, 2016, by Tarbet et al., U.S. Appl. No. 15/088,863.
U.S. Patent Application filed on Jan. 25, 2017, by Niedermeyer, U.S. Appl. No. 15/415,562.
U.S. Patent Application Filed on Sep. 22, 2015, by Neidermeyer, U.S. Appl. No. 14/861,375.
U.S. Patent Application Filed on Sep. 22, 2015, by Neidermeyer, U.S. Appl. No. 14/861,442.
Final Office Action received for U.S. Appl. No. 15/976,447, dated Jun. 16, 2020, 9 pages.
Final Office Action received for U.S. Appl. No. 16/012,508, dated Jun. 8, 2020, 24 pages.
Hopp Bela et al, "Production of nanostructures on bulk metal samples by laser ablation for fabrication of low-reflective surfaces", applied physics a materials science & processing, Springer Berlin Heidelberg, vol. 113, No. 2, Aug. 14, 2013, pp. 291-296.
International Search Report and Written Opinion received for PCT Patent Application No. PCT/US2020/041796, dated Oct. 7, 2020, 9 pages.
Thanaa Majied Al-Novi, "Antibacterial activity of Silver and Gold Nanoparticles against *Streptococus, Staphylococcus aureus and E. coli*", Al-Mustansiriya J. Sci, Vo. 23, No. 3, 2012.

\* cited by examiner

NANOPARTICLE COMPOSITIONS AND METHODS FOR TREATING OR PREVENTING TISSUE INFECTIONS AND DISEASES

CROSS-REFERENCE TO RELATED APPLICATIONS

This application is a division of U.S. patent application Ser. No. 15/088,863, filed Apr. 1, 2016, which claims the benefit of U.S. Provisional Patent Application No. 62/141,692, filed Apr. 1, 2015, and U.S. Provisional patent application Ser. No. 62/168,094, filed May 29, 2015, the disclosures of which are incorporated by reference in their entirety.

BACKGROUND

1. Field of the Invention

Disclosed herein are nanoparticle compositions and methods for treating or preventing tissue diseases or infections, such as dermatological conditions or MRSA, including stabilized multi-component antimicrobial nanoparticle compositions for dermal, subdermal, or subcutaneous applications, and methods for making and using such compositions.

2. Relevant Technology

A wide variety of dermatological and other tissue diseases affect humans and animals. These conditions can range from mild but annoying conditions to serious and even life threatening diseases. Additionally, some dermatological and other tissue diseases can negatively affect one's desired appearance and can lead to cosmetic concerns, both during the disease and even permanently afterwards as a result of scarring or other tissue damage.

For many tissue conditions or diseases, the root cause is related to microbial infection, such as infection caused by bacteria, viruses, or fungi. Treatment of these conditions or diseases is typically carried out by eliminating the underlying microbial cause. However, particularly in the case of bacteria-related or bacteria-caused conditions, where treatment calls for antibiotics, the treatment may have limited effectiveness because of microbial buildup of resistance or immunity to the available selection of antibiotics. In extreme cases, treatment may fail and an operation is required to cut away dead tissue. In addition, apart from natural immunity and acquired immunity from vaccinations, there are no compositions that can reliably target and selectively destroy viruses related to certain skin conditions.

One common dermatological condition is acne, which is typically the result of skin pores becoming blocked with oil and dead skin cells, creating an environment for bacteria to thrive and grow, thereby forming the acne. Though not life-threatening, acne is extremely widespread, can be painful, can cause emotional distress, and can cause permanent scarring affecting one's appearance.

Herpes labialis (cold sores), caused by a form of herpes simplex virus, is also a common dermatological condition. Although there is not yet a cure for herpes infection, outbreaks could be better managed through application of an effective antiviral to the sores, promoting faster healing and pain control.

Other dermatological conditions, such as abrasions, sores, lesions, or ulcers, may not necessarily have a root microbial cause but nevertheless become sites of potential infection and can lead to serious internal infections if not properly cared for. Thus, a prophylactic approach is often desired even before signs of any infection are present.

Some populations need to be particularly vigilant with respect to treatment of dermatological conditions. The elderly, the young, and those with compromised immune systems may be particularly susceptible to certain dermatological conditions. In addition, for such populations, even common dermatological infections or conditions can rapidly advance to serious medical conditions. Other at risk populations include diabetics, who often suffer from difficult to treat diabetic ulcers, and those who spend long periods of time in beds or wheelchairs, or who cannot move certain areas without help, putting them at risk for decubitus ulcers (bed sores).

Methicillin-resistant *Staphylococcus aureus* (MRSA) infections are caused by strains of *Staphylococcus aureus* which have developed resistance to beta-lactam antibiotics such as penicillins (e.g., methicillin, oxacillin, dicloxacillin, nafcillin) and cephalosporins. Such infections can be dangerous and difficult to treat due to the ineffectiveness of standard antibiotic treatments against them. In some cases, a relatively less dangerous MRSA infection, such as one beginning on the outer layers of the skin, can progress to deeper skin tissues, or to other tissues of the body, where it can cause further damage. If not controlled, such infections can lead to sepsis, toxic shock, and death.

MRSA infections often spread in crowded areas, such as hospitals, prisons, college dormitories, military stations, and gyms. Hospitals, in particular, are places where MRSA infections are of great concern. In hospitals, there is a higher concentration of those with weak or compromised immune systems who are at greater risk of contracting and suffering harm from a MRSA infection. In addition, those with serious MRSA infections are likely to end up at a hospital, where there is risk that nurses, doctors, equipment, and other potential vectors will contact the infected individual and spread the disease to other patients, hospital staff, or visitors of the hospital. Further, the inherent prevalence of open wounds and surgical sites, and the necessary use of invasive devices and procedures (catheter insertion, intravenous injections, etc.) create a multitude of infection routes for MRSA to potentially spread and become established.

Accordingly, there has been and remains a need to find reliable treatments and prophylactics for use in treating dermatological conditions and preventing infections of skin and other tissues, including MRSA infections of the skin and other tissues. Such treatments should be able to reliably kill or deactivate MRSA bacteria or other microbes causing the condition or putting one at risk for the condition without also causing unnecessary pain or undue harm to the subject being treated.

SUMMARY

Disclosed herein are nanoparticle compositions and treatment methods for treating or preventing a variety of tissue diseases or infections, including dermatological conditions, such as acne, cold sores, or fungal rashes, dermal Methicillin-resistant *Staphylococcus aureus* (MRSA) infections, and other MRSA infections.

Compositions and treatment methods may be used for treating tissue diseases or infections caused by microbes, such as bacterial, viral, and/or fungal infections, or for preventing the infection of a wound, such as a cut, abrasion, ulcer, lesion, sore, etc. The compositions and treatment methods disclosed herein may also be used as a prophylactic, and in some embodiments may be applied to otherwise healthy tissue in order to prevent or reduce the occurrence of a tissue disease or infection.

In some embodiments, metal nanoparticles can comprise spherical-shaped metal nanoparticles having a mean diameter and a particle size distribution wherein at least 99% of the metal nanoparticles have a particle size within 30% of the mean diameter, or within 20% of the mean diameter, or within 10% of the mean diameter and/or wherein at least 99% of the spherical-shaped nanoparticles have a diameter within ±3 nm of the mean diameter, or within ±2 nm of the mean diameter, or within ±1 nm of the mean diameter.

In some embodiments, metal nanoparticles can comprise coral-shaped metal nanoparticles having a non-uniform cross section and a globular structure formed by multiple, non-linear strands joined together without right angles. In some cases the coral-shaped metal nanoparticles can be used together with spherical-shaped metal nanoparticles (e.g., in order to potentiate the spherical-shaped metal nanoparticles).

In some embodiments, metal nanoparticles can comprises at least one metal selected from the group consisting of gold, platinum, silver, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof. Nanoparticles comprised of silver, gold, and mixtures and alloys thereof can be particularly effective.

In some embodiments, metal nanoparticles can comprise spherical-shaped metal nanoparticles and/or coral-shaped metal nanoparticles. In some embodiments the coral-shaped metal nanoparticles can be used together with spherical-shaped metal nanoparticles (e.g., in order to potentiate the spherical-shaped metal nanoparticles).

In some embodiments, nanoparticle compositions, such as multi-component nanoparticle compositions, include a stabilizing agent capable of holding the nanoparticles in solution while still maintaining the functionality of the nanoparticles.

In some embodiments, a method of treating a tissue disease or infection comprises: (1) applying a treatment composition comprising a carrier and metal nanoparticles onto or into a treatment area affected by a disease or infection, and (2) the treatment composition killing or deactivating the microbes underlying and/or causing the disease or infection.

In some embodiments, a method of preventing a tissue disease or infection comprises: (1) applying treatment composition comprising a carrier and metal nanoparticles onto or into a treatment area affected by a wound, sore, or other tissue disease or infection, and (2) the treatment composition killing or deactivating microbes present at or coming into contact with the tissue disease or infection.

In some embodiments, a method of preventing or reducing the severity or occurrence of a tissue disease or infection comprises: (1) applying treatment composition comprising a carrier and metal nanoparticles onto a treatment area, and (2) the treatment composition killing or deactivating microbes present at or coming into contact with the treatment area.

The treatment area can be, for example, a dermal region, and the treatment composition is administered topically to the dermal region. In other embodiments, the treatment area can be deeper skin tissue and/or other tissue, particularly in some applications for treating MRSA infections, and the treatment composition is administered by injection into the treatment area or into tissue nearby the treatment area. In other embodiments, the treatment area can be MRSA-infected respiratory tissue, and the treatment composition is administered by inhalation to the respiratory tissue.

In some embodiments, a method of preventing a tissue disease or infection comprises: (1) applying a treatment composition comprising a carrier and metal nanoparticles onto or into a medical device, (2) the treatment composition killing or deactivating MRSA bacteria and other microbes present at or coming into contact with the medical device or tissue nearby the medical device, the treatment composition thereby preventing the patient from acquiring the tissue disease or infection (e.g., MRSA).

These and other advantages and features of the invention will be set forth in part in the description which follows, and in part will become apparent to those skilled in the art upon examination of the following or may be learned by practice of the invention.

DETAILED DESCRIPTION OF THE PREFERRED EMBODIMENTS

Figure 1A:
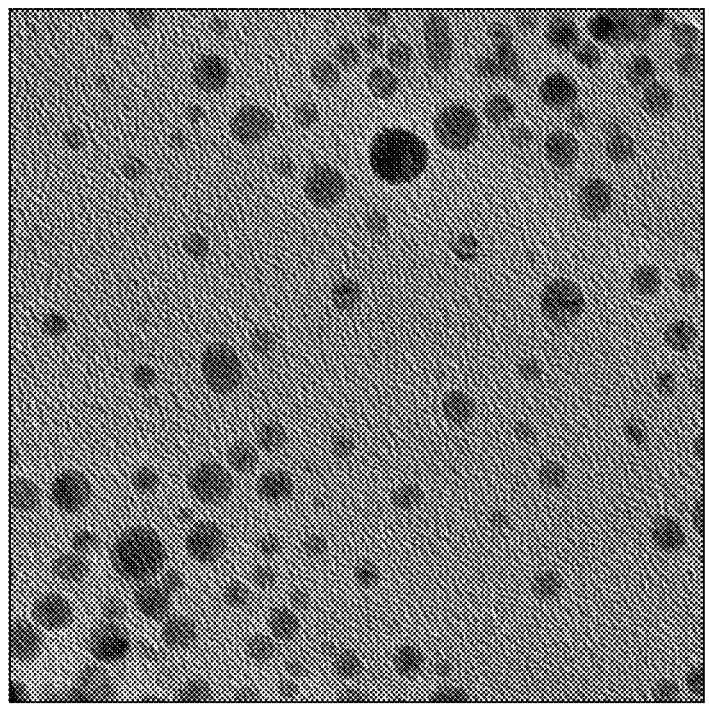
FIG. 1A is a scanning transmission electron microscope (STEM) image of exemplary spherical-shaped gold nanoparticles having substantially uniform size of about 14 nm, narrow particle size distribution, and showing no agglomeration of particles, the nanoparticles having use for making nanoparticle compositions for treating a tissue disease or infection.

Disclosed herein are nanoparticle compositions and methods for treating and preventing tissue diseases or infections, in particular those caused by microbes, such as viruses, bacteria, or fungi. Also disclosed herein are nanoparticle compositions and methods for preventing infection or further infection of wounds, sores, or other such diseases or infections. Also disclosed are methods for making and using such nanoparticle compositions. Included within the tissue diseases or infections treatable by one or more of the disclosed embodiments are MRSA infections of the dermal tissue. Also included within the disclosure are compositions and methods for treating MRSA infections that have infected other tissues, such as MRSA infections that have progressed beyond the dermal tissues or have originated in other tissues.

Unexpectedly, it has now been found that by selecting at least two differently configured nanoparticle components (e.g., different in size, shape, or both), each with specific particle size distribution, and stabilizing those at least two nanoparticle components with a stabilizing agent (such as natural-based polyphenol, cream, gel, or other surfactant), preferably one that is itself beneficial for use in dermal applications, it is possible to effectively target and preferentially kill or deactivate a specific type or types of microbes in the dermal region of humans and animals.

Tissue Disease Or Infection

Nanoparticle compositions and formulations disclosed herein can be formulated for treating tissue diseases or infections, such as those caused by microbes. For example, tissue diseases or infections caused by a viral infection and susceptible to treatment using the compositions and methods disclosed herein include cold sores, stomatitis sores, and other herpes lesions (caused by herpes simplex virus), and warts (caused by human papillomavirus).

Tissue diseases or infections caused by bacterial infection and susceptible to treatment using the compositions and methods disclosed herein include acne (caused or aggravated by a variety of skin bacteria), carbuncles (typically caused by *staphylococcus* bacteria), cellulitis (typically caused by *staphylococcus* and/or *streptococcus* bacteria), erysipelas (typically caused by *streptococcus* bacteria), impetigo (typically caused by *staphylococcus* and/or *streptococcus* bacteria), necrotizing fasciitis (typically caused by group A *Streptococcus* bacteria), and skin infections resulting from methicillin-resistant *Staphylococcus aureus* (MRSA).

MRSA infections are also known to affect other tissues in addition to dermal tissues, and are particularly known to reside in respiratory tissues. MRSA infections susceptible to treatment using the compositions and methods disclosed herein therefore include dermal infections, respiratory infections, septic and widespread infections, and other MRSA infections.

Tissue diseases or infections caused by fungal infection and susceptible to treatment using the compositions and methods disclosed herein include dermatophytosis infections such as tinea capitis, tinea barbae, tinea cruris, and tinea corporis (also known as "ringworm," and "athlete's foot," and caused by a variety of keratin feeding fungi species), fungal infections of the fingernails and toenails, seborrheic eczema (typically caused by *Malassezia* yeast), cutaneous candidiasis (typically caused by *Candida* yeast), and tinea versicolor (typically caused by *Pityrosporum ovale* yeast).

In some embodiments, a treatment may be applied even in the absence of any indication of infection in order to prevent an infection or worsening of a wound or dermatological condition. For example, in some circumstances, the skin and surrounding tissue may be free from infection, but may nevertheless be susceptible to infection. In many instances, cuts, lesions, and abrasions are susceptible to a variety of infections which can cause further damage to the skin and surrounding tissue as well as more distant tissues and organs of the body.

Those with weak or compromised immune systems are particularly susceptible to infections that enter the body via cuts, punctures, lesions, or the like and rapidly advance into a serious medical condition. In addition, even those with otherwise healthy immune systems may have wounds (e.g., post-surgical wounds or post-injury wounds) that remain exposed to infection risk until the skin is fully healed. Some wounds (e.g., diabetic and decubitus ulcers), due to the nature of the underlying condition, are difficult to heal and can remain exposed to potential infection for long periods of time.

In some embodiments, a treatment may be applied prophylactically even though the treatment area is healthy. For example, a treatment formulation may be applied to the face, neck, back, or other portion of a patient or user in order to prevent and/or lessen the occurrence of acne.

Nanoparticle Configurations

In some embodiments, the metal nanoparticles may comprise or consist essentially of nonionic, ground state metal nanoparticles. Examples include spherical-shaped metal nanoparticles, coral-shaped metal nanoparticles, or a blend of spherical-shaped metal nanoparticles and coral-shaped metal nanoparticles.

In some embodiments, metal nanoparticles useful for making nanoparticle compositions comprise spherical nanoparticles, preferably spherical-shaped metal nanoparticles having a solid core. The term "spherical-shaped metal nanoparticles" refers to nanoparticles that are made from one or more metals, preferably nonionic, ground state metals, having only internal bond angles and no external edges or bond angles. In this way, the spherical nanoparticles are highly resistant to ionization, highly stable, and highly resistance to agglomeration. Such nanoparticles can exhibit a high $\xi$-potential, which permits the spherical nanoparticles to remain dispersed within a polar solvent without a surfactant, which is a surprising and unexpected result.

In some embodiments, spherical-shaped metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less.

In some embodiments, spherical-shaped nanoparticles can have a particle size distribution such that at least 99% of the nanoparticles have a diameter within 30% of the mean diameter of the nanoparticles, or within 20% of the mean diameter, or within 10% of the mean diameter. In some embodiments, spherical-shaped nanoparticles can have a mean particle size and at least 99% of the nanoparticles have a particle size that is within ±3 nm of the mean diameter, ±2 nm of the mean diameter, or ±1 nm of the mean diameter. In some embodiments, spherical-shaped nanoparticles can have a $\xi$-potential of at least 10 mV, preferably at least about 15 mV, more preferably at least about 20 mV, even more preferably at least about 25 mV, and most preferably at least about 30 mV (all $\xi$-potential values are absolute values and are understood to be positive or negative).

Figure 1B:
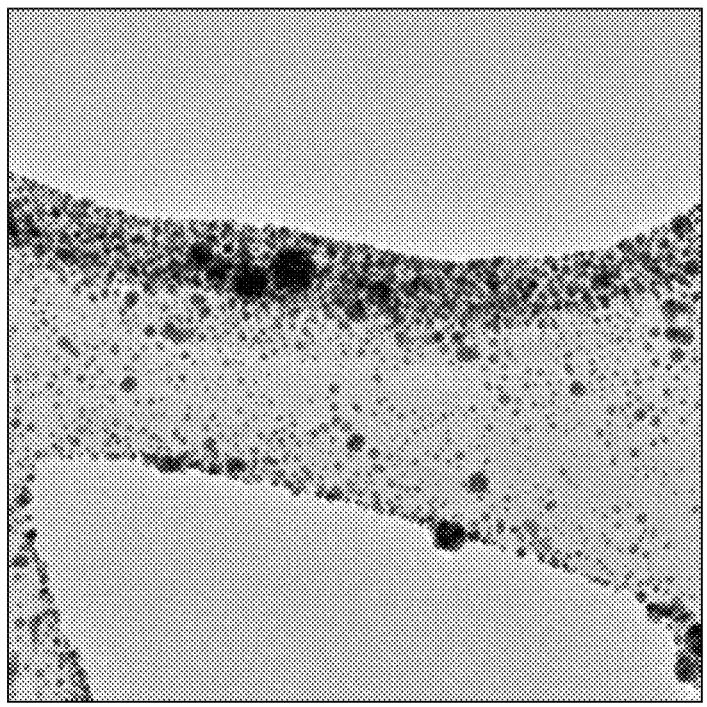
FIGS. 1B and 1C are scanning transmission electron microscope (STEM) images of exemplary spherical-shaped gold nanoparticles on a carbon lattice structure, the nanoparticles having substantially uniform size of about 14 nm, narrow particle size distribution, and showing no agglomeration of particles, the nanoparticles having use for making nanoparticle compositions for treating a tissue disease or infection.
Figure 1C:
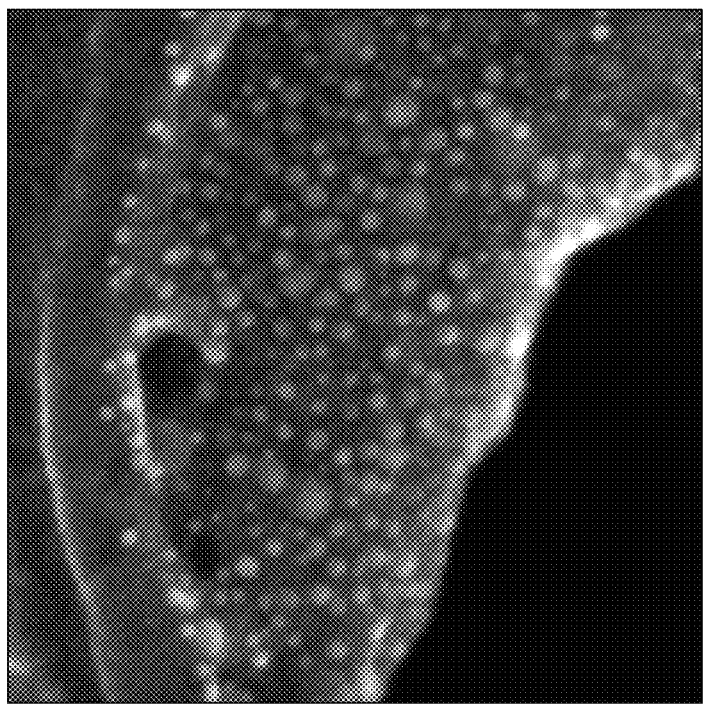
Figure 2A:
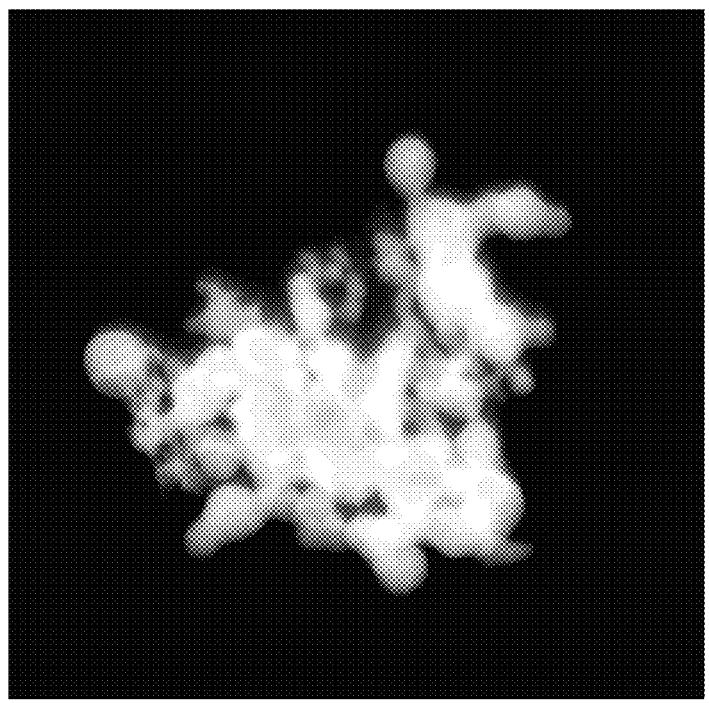
FIG. 2A is a scanning transmission electron microscope (STEM) image of an exemplary coral-shaped gold nanoparticle having a length of about 25 nm, showing no right angles or facets and having smooth curves at all intersections, the nanoparticle having use for making nanoparticle compositions for treating a tissue disease or infection.
Figure 2B:
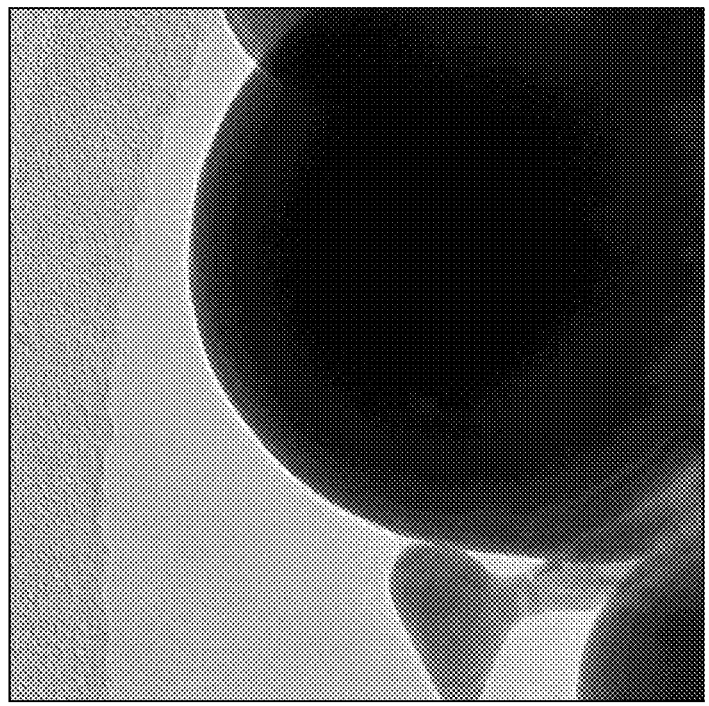
FIGS. 2B and 2C are scanning transmission electron microscope (STEM) images showing zoomed in views of an exemplary coral-shaped gold nanoparticles having a length of about 25 nm, showing no right angles or facets and having smooth curves at all intersections, also illustrating differing atomic structure at the edges than in the center of the particle showing shorter bond lengths to accomplish smoothness, the nanoparticles having use for making nanoparticle compositions for treating a tissue disease or infection.
Figure 2C:
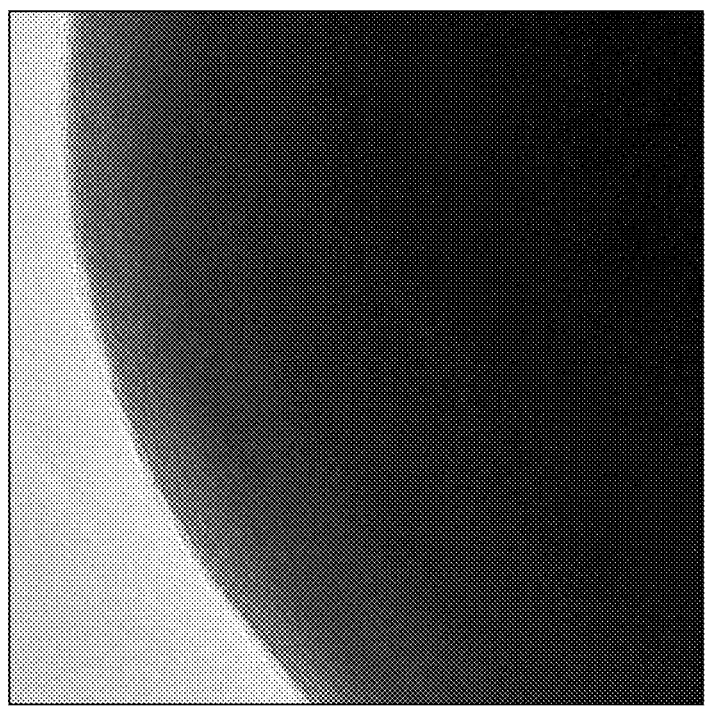

Examples of methods and systems for manufacturing spherical-shaped nanoparticles are disclosed in U.S. Patent Publication No. 2013/0001833 to William Niedermeyer, which is incorporated herein by this reference. FIG. 1 is a transmission electron microscope image (TEM) of exemplary spherical-shaped nanoparticles made using the methods and systems described in U.S. Patent Publication No. 2013/0001833. The illustrated nanoparticles are spherical-shaped silver (Ag) nanoparticles of substantially uniform size, with a mean diameter of about 10 nm and a narrow particle size distribution. In some embodiments, spherical-shaped nanoparticles can have a solid core rather than being hollow, as is the case with conventional metal nanoparticles, which are usually formed on the surfaces of non-metallic seed nanoparticles (e.g., silica), which are thereafter removed to yield hollow nanospheres.

In some embodiments, nonionic metal nanoparticles useful for making nanoparticle compositions may also comprise coral-shaped nanoparticles. The term "coral-shaped metal nanoparticles" refers to nanoparticles that are made from one or more metals, preferably nonionic, ground state metals having a non-uniform cross section and a globular structure formed by multiple, non-linear strands joined together without right angles. Similar to spherical-shaped nanoparticles, coral-shaped nanoparticles may have only internal bond angles and no external edges or bond angles. In this way, coral-shaped nanoparticles can be highly resistant to ionization, highly stable, and highly resistance to agglomeration. Such coral-shaped nanoparticles can exhibit a high ξ-potential, which permits the coral-shaped nanoparticles to remain dispersed within a polar solvent without a surfactant, which is a surprising result.

In some embodiments, coral-shaped nanoparticles can have lengths ranging from about 15 nm to about 100 nm, or about 25 nm to about 95 nm, or about 40 nm to about 90 nm, or about 60 nm to about 85 nm, or about 70 nm to about 80 nm. In some embodiments, coral-shaped nanoparticles can have a particle size distribution such that at least 99% of the nanoparticles have a length within 30% of the mean length, or within 20% of the mean length, or within 10% of the mean length. In some embodiments, coral-shaped nanoparticles can have a ξ-potential of at least 10 mV, preferably at least about 15 mV, more preferably at least about 20 mV, even more preferably at least about 25 mV, and most preferably at least about 30 mV (all ξpotential values are absolute values and are understood to be positive or negative).

Examples of methods and systems for manufacturing coral-shaped nanoparticles are disclosed in U.S. Patent Publication No. 2016/0082514 to William Niedermeyer, which is incorporated herein by this reference. FIGS. 2A-2E are transmission electron microscope images (TEMs) of exemplary coral-shaped metal nanoparticles made using the methods and systems disclosed in U.S. Patent Publication No. 2016/0082514. The illustrated nanoparticles are coral-shaped gold nanoparticles.

The metal nanoparticles, including spherical-shaped and coral-shaped nanoparticles, may comprise any desired metal, mixture of metals, or metal alloy, including at least one of silver, gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof.

According to some embodiments, spherical metal nanoparticles will comprise at least one of silver or gold. In the case of nanoparticles for use in treating dermatological conditions related to bacteria and fungi, the metal nanoparticles may primarily or exclusively comprise silver. However, in other embodiments, such as in the case of smaller metal nanoparticles for use in treating dermatological conditions caused by viruses, the metal nanoparticles may primarily or exclusively comprise gold. Due to the nature of silver and gold atoms making up the nanoparticles, it has been found that gold nanoparticles are typically better able to hold together at very small sizes (e.g., smaller than about 5-7 nm) compared to silver nanoparticles. On the other hand, a gold-silver alloy typically provides the particle stabilizing activity of gold and the higher microbe killing activity of silver. In some embodiments, coral-shaped nanoparticles are included and primarily or exclusively include gold nanoparticles.

Antimicrobial Activity

Figure 3:
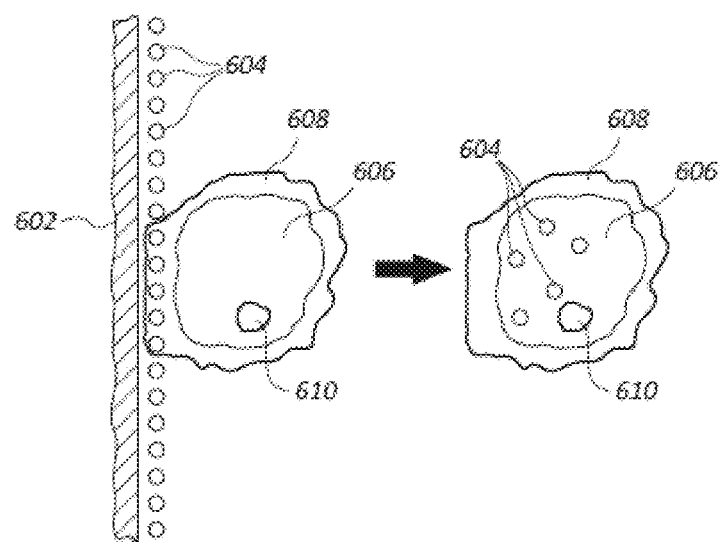
FIG. 3 schematically illustrates a microbe after having absorbed spherical-shaped metal nanoparticles.

FIG. 3 schematically illustrates a microbe 608 having absorbed spherical-shaped nanoparticles 604 from a solid substrate 602, such as by active absorption or other transport mechanism. Alternatively, spherical-shaped nanoparticles 604 can be provided in a composition (not shown), such as in a liquid, cream, or gel carrier. The nanoparticles 604 can freely move throughout the interior 606 of microbe 608 and come into contact with one or more vital proteins or enzymes 610 that, if denatured, will kill or disable the microbe.

Figure 4:
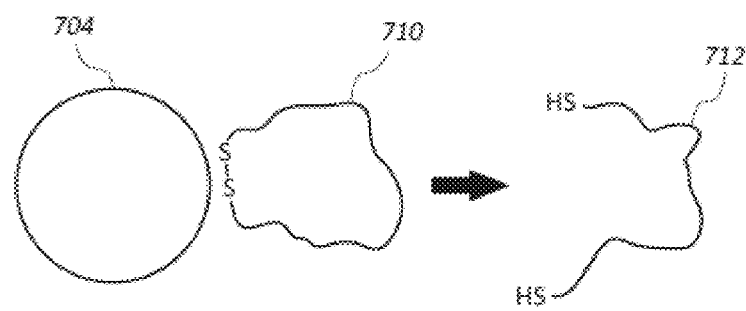
FIG. 4 schematically illustrates a microbe protein with disulfide bonds being catalytically denatured by an adjacent spherical-shaped nanoparticle.

One way that nanoparticles may kill or denature a microbe is by catalyzing the cleavage of disulfide (S—S) bonds within a vital protein or enzyme. FIG. 4 schematically illustrates a microbe protein or enzyme 710 with disulfide bonds being catalytically denatured by an adjacent spherical-shaped nanoparticle 704 to yield denatured protein or enzyme 712. In the case of bacteria or fungi, the cleavage of disulfide bonds and/or cleavage of other chemical bonds of vital proteins or enzymes may occur within the cell interior and thereby killing the microbe in this manner. Such catalytic cleavage of disulfide (S—S) bonds is facilitated by the generally simple protein structures of microbes, in which many vital disulfide bonds are exposed and readily cleaved by catalysis.

Another mechanism by which metal (e.g., silver) nanoparticles can kill microbes is through the production of active oxygen species, such as peroxides, which can oxidatively cleave protein bonds, including but not limited to amide bonds.

In the case of viruses, spherical-shaped and coral-shaped metal nanoparticles can alternatively deactivate viruses by attaching to glycoproteins and/or catalyzing protein denaturing reactions in the protein coat so that the virus is no longer able to attach to a host cell and/or inject genetic material into the host cell. Because very small nanoparticles can pass through a virus, denaturing of the protein coat may occur within the interior of the virus. A virus that is rendered unable to attach to a host cell and/or inject genetic material into the host cell is essentially inactive and no longer pathogenic.

Figure 5:
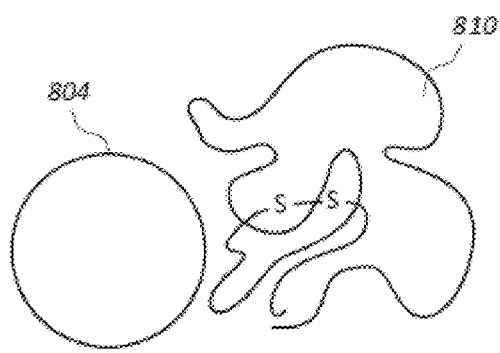
FIG. 5 schematically illustrates a mammalian protein with disulfide bonds that are shielded so as to resist being catalytically denatured by an adjacent spherical-shaped nanoparticle.

Notwithstanding the lethal nature of nonionic metal nanoparticles relative to microbes, they can be relatively harmless to humans, mammals, and healthy mammalian cells, which contain much more complex protein structures compared to simple microbes in which most or all vital disulfide bonds are shielded by other, more stable regions of the protein. FIG. 5 schematically illustrates a mammalian protein 810 with disulfide (S—S) bonds that are shielded so as to resist being catalytically denatured by an adjacent spherical-shaped nanoparticle 804. In many cases the nonionic nanoparticles do not interact with or attach to human or mammalian cells, remain in and follow fluid flow, do not cross barriers, remain in the vascular system, and can be quickly and safely expelled through the urine without damaging kidneys or other cells.

In the particular case of silver (Ag) nanoparticles, the interaction of the silver (Ag) nanoparticle(s) within a microbe has been demonstrated to be particularly lethal without the need to rely on the production of silver ions (Ag⁺) to provide the desired antimicrobial effects, as is typically the case with conventional colloidal silver compositions. The ability of silver (Ag) nanoparticles to provide effective microbial control without any significant release of toxic silver ions (Ag⁺) into the surrounding environment is a substantial advancement in the art.

Targeted Nanoparticles

In some embodiments, anti-viral compositions comprise metal nanoparticles having a particle size of about 8 nm or less, or about 1 nm to about 7 nm, or about 2 nm to about 6.5 nm, or about 3 nm to about 6 nm. In some embodiments, anti-bacterial compositions can include metal nanoparticles having a particle size of about about 3 nm to about 14 nm, or about 5 nm to about 13 nm, or about 7 nm to about 12 nm, or about 8 nm to about 10 nm. In some embodiments, anti-fungal compositions can include metal nanoparticles having a particle size of about 9 nm to about 20 nm, or about 10 nm to about 18 nm, or about 11 nm to about 16 nm, or about 12 nm to about 15 nm. Within any of the foregoing size ranges, it is possible to select "designer antimicrobial particles" of specific size that are particularly effective in targeting a specific microbe.

The ability to select and use microbe-specific nanoparticles provides a number of benefits. For example, in the case where only certain nanoparticle sizes are effective in killing a particular microbe or class of microbes and/or treating certain tissue diseases or infections, providing metal nanoparticles within a narrow particle size distribution of the correct particle size maximizes the proportion of nanoparticles that are effective in killing the target microbe and minimizes the proportion of nanopartricles that are less effective, or ineffective, in killing the target microbe. This, in turn, greatly reduces the overall amount or concentration of nanoparticles required to provide a desired kill or deactivation rate of a targeted microbe. Eliminating improperly sized nanoparticles also reduces the tendency of the composition to kill or harm non-targeted microbes or other cells. In this way, highly specific antimicrobial compositions can better target a harmful microbe and/or dermatological condition while being less harmful or even non-toxic to humans and animals.

The size of the nanoparticles can be selected to target and selectively kill specific types of microbes associated with a tissue disease or infection. For example, the nanoparticles can have a particle size in a range of about 1 nm to about 25 nm, or about 2 nm to about 15 nm, or about 2 nm to about 7 nm, or about 3 nm to about 6 nm, or about 7 nm to about 11 nm, or about 11 nm to about 14 nm.

By way of further example, nanoparticles having a diameter of less than about 9 nm (e.g., 1-7 nm or 3-6 nm) have been found to be effective in killing viruses, nanoparticles having a diameter of about 7 nm to about 12 nm (e.g., 8-10 nm) have been found to be effective in killing bacteria, and nanoparticles having a diameter of about 12 nm to about 18 nm (e.g., 12-15 nm) have been found to be effective in killing fungi. Within the foregoing ranges, there may be specific sizes of nanoparticles that are most effective in killing a particular type of virus, bacteria, or fungus.

In some embodiments, compositions and treatment methods may be selected based on a particular type of microbe (e.g., virus, bacteria, fungus) known to cause or be associated with the targeted tissue disease or infection or with the disease or infection desired to be prevented. For example, treatments of bacterial diseases or infections (e.g., acne) and/or MRSA infections may be selected and tailored with nanoparticles having a diameter of about 7 nm to about 12 nm (e.g., 8-10 nm) in order to effectively kill and/or prevent the growth of the condition causing and/or condition aggravating bacteria. In a further example, treatments of tissue diseases or infections associated with a viral infection (e.g., herpes) may be selected and tailored with nanoparticles having a diameter of less than about 9 nm (e.g., 1-7 nm or 3-6 nm) in order to neutralize the viral agent. In a further example, treatments of tissue diseases or infections associated with fungi (e.g., dermatophytosis infections) may be selected and tailored with nanoparticles having a diameter of about 12 nm to about 18 nm (e.g., 12-15 nm) in order to kill the fungal infection.

Multi-Component Nanoparticle Compositions

In some embodiments, coral-shaped metal nanoparticles can be used in conjunction with spherical-shaped metal nanoparticles. In general, spherical-shaped metal nanoparticles can be smaller than coral-shaped metal nanoparticles and in this way can provide very high surface area for catalyzing desired reactions or providing other desired benefits. On the other hand, the generally larger coral-shaped nanoparticles can exhibit higher surface area per unit mass compared to spherical-shaped nanoparticles because coral-shaped nanoparticles have internal spaces and surfaces rather than a solid core and only an external surface. In some cases, providing nanoparticle compositions containing both spherical-shaped and coral-shaped nanoparticles can provide synergistic results. For example, coral-shaped nanoparticles can help carry and/or potentiate the activity of spherical-shaped nanoparticles in addition to providing their own unique benefits.

In some embodiments, a nanoparticle composition includes both spherical-shaped and coral-shaped nanoparticles. In some embodiments, the mass ratio of spherical-shaped nanoparticles to coral-shaped nanoparticles in the nanoparticle composition can be in a range of about 1:1 to about 50:1, or about 2.5:1 to about 25:1, or about 5:1 to about 20:1, or about 7.5:1 to about 15:1, or about 9:1 to about 11:1, or about 10:1. The particle number ratio of spherical-shaped nanoparticles to coral-shaped nanoparticles in the nanoparticle composition can be in a range of about 10:1 to about 500:1, or about 25:1 to about 250:1, or about 50:1 to about 200:1, or about 75:1 to about 150:1, or about 90:1 to about 110:1, or about 100:1.

In some embodiments, a nanoparticle composition includes: (1) a first set of metal nanoparticles having a specific particle size and a particle size distribution, (2) and second set of metal nanoparticles having a specific particle size and a particle size distribution with at least one of either the first or second set of metal nanoparticles selected so as to selectively and preferentially kill one of a virus, bacterium, or fungus, (3) a stabilizing agent, and (4) a carrier, which carrier may be the stabilizing agent itself or may be comprised of one or more other components for delivery of the multicomponent nanoparticles onto and ultimately into the dermal or sub-dermal region of a person or animal.

Because of the extremely small size and spherical shaped of the nanoparticles it is believed that these particles are absorbed into and move quickly through the dermal or sub-dermal region of an animal or human. Unexpectedly, while the coral-shaped nanoparticles alone have not exhibited significant antimicrobial efficacy, the inclusion of these particles in conjunction with specifically sized spherical nanoparticles has provided increased efficacy for the spherical particles, particularly in dermal and or sub-dermal applications.

In some embodiments, the compositions will include at least one spherical-shaped anti-microbial nanoparticle component and larger coral-shaped nanoparticle component. In these embodiments, the at least one selected spherical-shaped nanoparticle component will be present in the solution in a range of between about 1 and about 15 ppm (e.g., at least 1 and at mostly ppm) and more particularly in the range of between bout 1 and about 5 ppm (e.g., at least 1 and at most 5 ppm). Additionally, in some embodiments, the larger coral-shaped nanoparticles will be present in the solution in a range of between about 1 and about 5 ppm (e.g., at least 1 and at most 5 ppm) and more particularly between about 1 and about 3 ppm (e.g., at least 1 and at most 3 ppm). It should be understood that the upper concentration is not restricted as much by efficacy as by product formulation cost. Thus, in other embodiments, the spherical-shaped nanoparticle component may present at a concentration above 5 ppm and/or the coral-shaped nanoparticle component may be present at a concentration above 3 ppm.

Stabilizing Agents & Carriers

Some embodiments may include a stabilizing agent. For example, there are times when it is desirable to have different specifically sized nanoparticles within the same solution to take advantage of each of the different properties and effects of the different particles. However, when differently sized particles are mixed into a single solution, the overall long-term stability of these particles within that single solution may be substantially diminished as a result of unequal forces exerted on the various particles causing eventual agglomeration of the particles. This phenomenon may become even more pronounced when that solution is either heated or cooled significantly above or below standard room temperature conditions.

The stabilizing agent may itself be beneficial for use in dermal, or sub-dermal, or sub-cutaneous applications. Examples of stabilizing agents include alcohols generally (e.g., ethanol, propanol, butanol, etc.), as alcohols have been observed to effectively maintain nanoparticles of different sizes and different shapes within a given solution. A more particular example of stabilizing agents include polyphenols (e.g., natural-based polyphenols such as arjuna bark extract, grape seed extract, etc.) which can have particular advantages in applications to skin or other tissue and which have shown good nanoparticle stabilization results. Triglycerides such as grape seed oil, coconut oil, and the like, and other oils such as lavender and other terpenes may be used as stabilizing agent or part of the stabilizing agent. In addition, amine compounds such as mono-, di-, and tri-ethanol amine, and carbohydrates such as sucrose, fructose, and higher polymers also have the ability to stabilize multi-component nanoparticle compositions and can be used as stabilizing agent or part thereof.

Stabilizing agents such as natural-based polyphenols (which would include compounds such as grape seed oil, grape seed extract (water soluble portion), arjuna bark extract, ethanol amines, or any other water soluble polyphenol sources and the like), can be dissolved into a carrier (e.g., water, alcohol, water alcohol combination, or any other carrier described herein). Natural-based polyphenols typically show good efficacy when dissolved within a carrier in the micro- to milli-molar concentration range with the upper range limitation typically being constrained not by efficacy but by product cost.

Additional examples of stabilizing agents include liposomes, creams, and other emulsions. These and similar examples can stabilize the multi-component nanoparticle compositions while constituting the majority of the overall composition, which overall composition may contain little or no water or alcohol or other liquid-phase components.

The utilization of gels, creams, and the like that are readily absorbed through the dermal layer further facilitates transport of the nanoparticles into that dermal layer where the antimicrobial effects of those nanoparticles can be achieved.

These various stabilizing agents have the capacity to hold the at least two differently sized and/or shaped nanoparticles in suspension and deliver these nanoparticles into the dermal region of a person or animal without so powerfully retaining the nanoparticles so as to diminish the antimicrobial properties of the nanoparticles.

The specific stabilizing agent or combination of stabilizing agents may be chosen depending on the precise dermal condition being treated or prophylactically prevented. For example, in open wound applications, a simple aqueous solution with a stabilizing agent and the appropriate nanoparticles may be preferable over a composition based on a cream.

Given the ability of many of these stabilizing agents to readily dissolve into water, alcohols and/or oils, introduction or manufacture of the particles into solution with the stabilizing agents allows the multi-component nanoparticles to be readily incorporated into any number of carriers that may then become the basis for a wide array of products including simple dermal sprays, creams, and wiping solutions, for example.

Thus, in some embodiments, the nanoparticle composition may also include a carrier, or the stabilizing agent may itself function as a carrier, for delivering the metal nanoparticles onto the skin or onto a dermatological or other tissue treatment site. The carrier can be a liquid, gel, or solid. Some carriers may be more suitable than others depending on the disease, infection, condition, or skin type being treated. For example, the solubility characteristics of the carrier can be selected to maximize or otherwise provide a desired diffusion throughout a treated area and/or another portion of the skin or surrounding tissue in contact with the treated area.

Examples of compounds that can be utilized for application to tissue and can be used as carriers to formulate nanoparticle compositions in accordance to the present invention either in conjunction with one or more separate stabilizing agents or as the stabilizing agent include, but are not limited to, water, alcohols, ketones, esters, citrus oils, essential oils, vegetable and other plant and natural oils, triglycerides, ethers, organic solvents, methanol, ethanol, isopropyl alcohol, other alcohols, glycols, glycerin, polyols, 1,3-propandiol, petroleum jelly, waxes, polymers, polymerizable materials, and surfactants.

In one preferred embodiment the carrier is a cream. For example the carrier may be comprised of a stearic acid cream base optionally containing oils such as coconut or olive oil, grape seed oil, and/or vitamin E oil along with an emulsifying wax which carrier composition also acts as a stabilizing agent to maintain the multicomponent nanoparticles within the cream composition.

In other embodiments the carrier is a water or combined water and alcohol solution which may itself contains a micro to millimolar concentration of a separate stabilizing agent dissolved into the carrier so as to maintain the multicomponent nanoparticles within the overall composition.

Gels known in the art can be used as carriers, such as gels containing one or more of the foregoing liquid components together with known gelling agents. Gel compositions can more easily adhere to a living or non-living substrate being treated.

Various stabilizing agents and carriers as disclosed herein have demonstrated the capacity to hold the at least two differently sized and shaped nanoparticles in suspension and thereby deliver these nanoparticles into the dermal region of a person or animal without so powerfully retaining the nanoparticles so as to diminish the antimicrobial properties of the nanoparticles.

In some embodiments, a nanoparticle composition can be formulated so that the metal nanoparticles are included in a concentration so that a measured quantity of the nanoparticle composition, when applied onto the skin or onto or into a tissue treatment site, will provide a predetermined concentration or quantity of metal nanoparticles and/or will provide ongoing antimicrobial efficacy for an extended period of time. The nanoparticle composition can have a higher concentration of nanoparticles that become diluted when mixed with other liquids applied to or naturally contained on or within the skin or other tissue treatment site. Depending on the skin or tissue treatment site, the nature of the nanoparticles being added, and the type of carrier being used, the nanoparticle composition may contain about 0.5 ppm to about 100 ppm of metal nanoparticles by weight, or about 1 ppm to about 50 ppm, or about 2 ppm to about 25 ppm, or about 3 ppm to about 20 ppm metal nanoparticles by weight.

In some embodiments, the nanoparticle composition can also include one or more optional components or adjuvents to provide desired properties, including, but not limited to antimicrobial agents, skin conditioners, plant extracts (e.g., arjuna bark extract, grape seed extract), astringents (e.g., witch hazel), moisturizers, emollients, antiseptics, salicylic acid, glypoic complex, azelaic acid, elemental sulfur, allantoin, benzoyl peroxide, etc.

Exemplary carriers for nasal or pulmonary aerosol or inhalation administration (e.g., for treating a respiratory MRSA infection or pneumonia) include solutions in saline which can contain, for example, benzyl alcohol or other suitable preservatives, absorption promoters to enhance bioavailability, and/or other solubilizing or wetting or dispersing agents, such as glycerin, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); and glycoaminoglycans and glycosaminoglycan-like compounds (e.g., hyaluronic acid), for example. In some embodiments, the nanoparticles and additional stabilizing agents and/or carriers are formulated as dry powders (e.g., powders useful for administering with dry powder inhalers).

Exemplary aerosols useful for nasal and/or inhalation administration (e.g., for treating a respiratory MRSA infection) can include a vaporizable propellant, such as low molecular weight hydrofluorocarbons or hydrocarbons that are liquid when constrained in a suitable container and are biocompatible and non-irritating). Ingredients such as water, alcohol, propylene glycol, and polyethylene glycols can be additionally included. Other embodiments, also useful for nasal and/or inhalation administration, may be provided as sprays (e.g., omitting an aerosol propellant). Such spray formulation may be provided as a solution, suspension, or emulsion capable of forming a fine mist for administration, and in some embodiments, may include saline and/or be isotonic.

Exemplary injectable solutions (e.g., for treating an internal MRSA infection) can include an aqueous emulsion or oleaginous suspension or saline solution (e.g., isotonic, hypotonic, or hypertonic, optionally including dextrose and/ or other electrolytes or additives). Such compositions can also include suitable dispersing or wetting agents. The sterile injectable preparation may also be formed in a non-toxic parenterally acceptable diluent or solvent, such as a solution in 1,2-propanediol (propylene glycol). Additional examples include solutions or suspensions which can contain, for example, suitable non-toxic diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Treatment Methods

In some embodiments, a method of treating a tissue disease, condition or infection comprises: (1) applying a treatment composition onto or into a treatment site, and (2) the treatment composition killing or deactivating the microbes underlying and/or causing the tissue disease, condition or infection.

In some embodiments, a method of preventing a tissue disease, condition or infection, such as a wound, cut, sore, ulcer, abrasion, lesion, or the like, comprises: (1) applying a treatment composition onto or into a treatment area affected by a wound or other condition, and (2) the treatment composition killing or deactivating microbes present at or coming into contact with the wound or other condition.

In some embodiments, a method of preventing or reducing the severity or occurrence of a tissue disease, condition or infection comprises: (1) applying a treatment composition onto or into a treatment area, and (2) the treatment composition killing or deactivating microbes present at or coming into contact with the treatment area.

In some embodiments, a method of treating a MRSA infection comprises: (1) administering a treatment composition comprising a carrier and metal nanoparticles onto and/or into tissue affected by a MRSA infection, and (2) the treatment composition killing or deactivating the MRSA bacteria underlying and/or causing the infection.

The preferred mode or combination of modes of administration may depend on the type, progression, and/or location of MRSA or other tissue infection. For example, treatment of a MRSA infection confined to the outer layers of skin may include topical administration, whereas treatment of a MRSA infection that has progressed to deeper layers of skin (e.g., in the form of abscesses or ulcers), or that resides or has spread to other tissues (e.g., bones and joints, as well as other tissues and organs) may include administration by injection. Treatment of sepsis resulting from a MRSA infection may include intravenous injection of the nanoparticle composition. In another example, treatment of a MRSA infection that resides in or has progressed to respiratory tissue such as lungs, throat, mouth, nasopharynx, esophagus, and trachea tissue may include administration by spray (e.g., nasal spray) and/or inhalation.

In some embodiments, a method of preventing a MRSA infection comprises: (1) applying a treatment composition comprising a carrier and metal nanoparticles onto or into a treatment area affected by a wound, sore, lesion, abscess, or surgical site, or to a treatment area as preparation for a surgical procedure; and (2) the treatment composition killing or deactivating MRSA bacteria coming into contact with the treatment area.

In some embodiments, a method of preventing a MRSA infection comprises: (1) applying a treatment composition comprising a carrier and metal nanoparticles onto or into a medical device, and (2) the treatment composition killing or deactivating MRSA bacteria present at or coming into contact with the medical device or tissue nearby the medical device, the treatment composition thereby preventing the patient from acquiring a MRSA infection.

When nanoparticle compositions are administered prophylactically (e.g., prior to or during a surgical or other medical procedure), they may be applied to the patient using any of the modes of administration disclosed above. Additionally, or alternatively, one or more medical devices used during a surgical or medical procedure may be contacted with a nanoparticle composition in order to prevent MRSA bacteria or other microbes from contacting the medical device and potentially infecting the patient. For example, catheters, intravenous lines, implants, scalpels and other medical tools, wound dressings, and other medical devices can be treated with nanoparticle compositions in order to kill any MRSA bacteria or other microbe on or coming into contact with the device.

The treatment composition may include spherical-shaped nanoparticles, coral-shaped nanoparticles, or both. In preferred embodiments, the treatment composition is a multi-component composition including a spherical-shaped nanoparticle component, a coral-shaped nanoparticle component, and a stabilizing agent.

In some embodiments, the treatment is repeated one or more times, or a subsequent, different treatment or combination of treatments is subsequently applied. For example, a treatment may an increasing or decreasing nanoparticle exposure, such as having a progressively changing nanoparticle concentration with each application to the treatment site. The time period between applications may also be established. For example, a nanoparticle composition may be applied weekly, every few days (e.g., five, four, three), every other day, daily, or multiple times per day (e.g., about ten, eight, six, four, or two times per day, or about every hour). In other embodiments, the nanoparticle composition may be applied as needed.

In some embodiments, a method of treating or preventing a disease, condition or infection associated with a virus comprises: (1) applying a treatment composition comprising an aqueous solution onto a treatment site of a human or animal containing a virus or at risk of contracting a virus, the treatment composition having (i) between about 1 and about 10 ppm of a group of spherical metal nanoparticles having a particle size of about 8 nm or less, or about 1 nm to about 7 nm, or about 2 nm to about 6.5 nm, or about 3 nm to about 6 nm, (ii) between about 1 and 10 ppm of a second group of coral metal nanoparticles having a particle size between 40 and 100 nm and (iii) a milli molar or micro molar concentration of a stabilizing agent (e.g., grape seed extract), and (2) the treatment composition deactivating the virus.

In some embodiments, a method of treating or preventing a disease, condition or infection associated with a bacteria comprises: (1) applying a treatment composition comprising an aqueous solution onto a treatment site of a human or animal containing a bacterium or at risk of contracting a bacterium, the treatment composition having (i) between about 1 and about 10 ppm of a group of spherical metal nanoparticles having a particle size of about 8 nm or less, or about 3 nm to about 14 nm, or about 5 nm to about 13 nm, or about 7 nm to about 12 nm, or about 8 nm to about 10 nm, (ii) between about 1 and 10 ppm of a a second group of coral metal nanoparticles having a particle size between 40 and 100 nm, and (iii) a milli molar or micro molar concentration of a stabilizing agent (e.g., grape seed extract), and (2) the anti-bacterial composition killing the bacterium.

In some embodiments, a method of treating or preventing a disease, condition or infection associated with a fungus comprises: (1) applying a treatment composition comprising an aqueous solution onto a treatment site of a human or animal containing a fungus or at risk of contracting a fungus, the treatment composition having (i) between about 1 and about 10 ppm of a group of spherical metal nanoparticles having a particle size of about 9 nm to about 20 nm, or about 10 nm to about 18 nm, or about 11 nm to about 16 nm, or about 12 nm to about 15 nm, (ii) between about 1 and 10 ppm of a second group of coral metal nanoparticles having a particle size between 40 and 100 nm and (iii) a milli molar or micro molar concentration of a stabilizing agent (e.g., grape seed extract), and (2) the anti-fungal composition killing the fungus.

Methods of Manufacture

The preferred embodiment for manufacturing the stabilized multi-component antimicrobial nanoparticle compositions requires manufacturing both nanoparticle components (e.g., in embodiments including two separate nanoparticle components) in liquids that are compatible with the final composition.

For example, in the case of a water, alcohol, or water and alcohol based composition, both the first and second nanoparticle components are manufactured in a water, alcohol, or water and alcohol based solution, and the stabilizing agent is then added to one or both of the nanoparticle components and the nanoparticle components can then be combined to achieve the desired concentrations.

In another example, such as in an embodiment having a cream based composition, the first and second nanoparticle components can be either manufactured into one of the major components of the final composition or made in a water or alcohol (or water alcohol mixture) and diluted into the cream based composition.

For example, stearic acid and oils and emulsifying wax and other minor components may be heated to between 160 and 200° F. in order to create the desired final composition. After this nearly completed cream composition has cooled to under preferably about 105° F., first and second sets of nanoparticles which have preferably been manufactured into a natural-based polyphenol can then be added to complete the final cream composition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Example 1

A stabilized multicomponent solution for treating a tissue disease, infection or condition is prepared and includes a 50% water 50% isopropyl alcohol solution having (i) 0.5 ppm spherical gold (Au) nanoparticles with a mean diameter of 10 nm with 99% of these Au nanoparticles having a diameter within ±1 nm of that mean diameter, (ii) 1 ppm of spherical silver (Ag) nanoparticles with a mean diameter of 8 nm with 99% of these Ag nanoparticles having a diameter within ±1 nm of that mean diameter, and (iii) arjuna bark extract at one micro molar concentration. This stabilized multicomponent antimicrobial solution is readily applied topically to any dermal or other tissue region having a microbial infection or at risk of developing an infection, disease or condition.

Example 2

A stabilized multicomponent antimicrobial solution for dermal or sub-dermal application is prepared and includes a 90% water 10% isopropyl alcohol solution having (i) 1 ppm coral shaped gold (Au) nanoparticles with a mean length of 40 nm with 99% of these Au nanoparticles having a cross section within ±6 nm of that mean length, (ii) 2 ppm of spherical silver (Ag) nanoparticles with a mean diameter of 10 nm with 99% of these Ag nanoparticles having a diameter within ±1 nm of that mean diameter, and (iii) grape seed extract at 1 milli molar concentration. This stabilized multicomponent antimicrobial solution is readily topically applied to any dermal or other tissue region containing a microbial infection or at risk of developing an infection, disease or condition.

Example 3

A stabilized multicomponent antimicrobial solution for dermal or sub-dermal application is prepared and includes a 30% water 70% isopropyl alcohol solution having (i) 3 ppm coral shaped gold (Au) nanoparticles with a mean length of 80 nm with 99% of these Au nanoparticles having a cross section within ±10 nm of that mean length, (ii) 5 ppm of spherical silver (Ag) nanoparticles with a mean diameter of 15 nm with 99% of these Ag nanoparticles having a diameter within ±1.5 nm of that mean diameter, and (iii) 1 milli molar concentration of an anionic detergent. This stabilized multicomponent solution is readily topically applied to any dermal or other tissue region containing a microbial infection or at risk of developing an infection, disease or condition, particularly fungal infections, diseases or conditions.

Example 4

A cream based carrier suitable for carrying a multicomponent antimicrobial composition is prepared by heating stearic acid, olive oil, and emulsifying wax to between 160 and 200° F. Nanoparticles are suitably added after cooling the composition to about 105° F.

Example 5

A stabilized multicomponent antimicrobial solution for dermal or sub-dermal application is prepared by adding to the cream carrier of Example 4 (i) 1 ppm coral shaped gold (Au) nanoparticles with a mean length of 80 nm with 99% of these Au nanoparticles having a length within ±10 nm of that mean cross section and (ii) 2 ppm of spherical silver (Ag) nanoparticles with a mean diameter of 15 nm with 99% of these Ag nanoparticles having a diameter within ±1.5 nm of that mean diameter and (iii) 1 millimolar concentration of grape seed oil into which both the Ag and Au nanoparticles are added before the grape seed oil was added to the overall product. This stabilized multicomponent antimicrobial solution is readily applied to any dermal or other tissue region containing a microbial infection or at risk of developing an infection, disease or condition and is particularly useful against fungal infections, diseases, or conditions.

Example 6

A stabilized multicomponent antimicrobial solution for dermal application is prepared by adding to the cream carrier of Example 4 (i) 3 ppm coral shaped gold (Au) nanoparticles with a mean length of 80 nm with 99% of these Au nanoparticles having a cross section within ±10 nm of that mean length and (ii) 5 ppm of spherical silver (Ag) nanoparticles with a mean diameter of 10 nm with 99% of these Ag nanoparticles having a diameter within ±1 nm of that mean diameter and (iii) 1 millimolar concentration of grape seed oil into which both the Ag and Au nanoparticles were added before the grape seed oil is added to the overall product. This stabilized multicomponent antimicrobial solution is readily applied topically to any dermal or other tissue region containing a microbial infection or at risk of developing an infection, and is particularly useful against bacterial infections, diseases or conditions.

Example 7

A stabilized multicomponent antimicrobial solution for dermal application is prepared by adding to the cream carrier of Example 4 (i) 3 ppm coral shaped gold (Au) nanoparticles with a mean length of 80 nm with 99% of these Au nanoparticles having a cross section within ±10 nm of that mean length and (ii) 3 ppm of spherical silver (Ag) nanoparticles with a mean diameter of 10 nm with 99% of these Ag nanoparticles having a diameter within ±1 nm of that mean diameter and (iii) 3 ppm of spherical Ag nanoparticles with a mean diameter of 15 nm with 99% of these Ag nanoparticles having a diameter within ±1.5 nm of that mean diameter and (iv) 1 millimolar concentration of arjuna bark extract into which both the Ag and Au nanoparticles are added before the arjuna bark extract is added to the overall product. This stabilized multicomponent antimicrobial solution is readily applied to any dermal or other tissue region containing a combination of actual or potential microbial infections, diseases or conditions and is particularly useful against bacterial and fungal infections, diseases or conditions.

Example 8

A stabilized multicomponent antimicrobial solution for dermal or sub-dermal application is prepared and includes a 50% water 50% ethanol solution having (i) 0.5 ppm spherical gold (Au) nanoparticles with a mean diameter of 10 nm with 99% of these Au nanoparticles having a diameter within ±1 nm of that mean diameter, (ii) 1 ppm of spherical silver (Ag) nanoparticles with a mean diameter of 8 nm with 99% of these Ag nanoparticles having a diameter within ±1 nm of that mean diameter, (iii) 10 ppm arjuna bark extract, and (iv) 10 ppm witch hazel. This stabilized multicomponent antimicrobial solution is readily applied to any dermal or other tissue region containing an infection, disease or condition or at risk of developing an infection, disease or condition.

Example 9

A stabilized multicomponent antimicrobial solution for dermal application is prepared and includes a 30% water 70% ethanol solution having (i) 1 ppm coral shaped gold (Au) nanoparticles with a mean length of 40 nm with 99% of these Au nanoparticles having a cross section within ±6 nm of that mean length, (ii) 2 ppm of spherical silver (Ag) nanoparticles with a mean diameter of 10 nm with 99% of these Ag nanoparticles having a diameter within ±1 nm of that mean diameter, (iii) 30 ppm arjuna bark extract, and (iv) 30 ppm witch hazel. This stabilized multicomponent antimicrobial solution is readily applied to any dermal or other tissue region containing an infection or at risk of developing an infection, disease or condition.

Example 10

A stabilized multicomponent antimicrobial solution for dermal application is prepared and includes a 70% water 30% ethanol solution having (i) 3 ppm coral shaped gold (Au) nanoparticles with a mean length of 80 nm with 99% of these Au nanoparticles having a cross section within ±10 nm of that mean length and (ii) 5 ppm of spherical silver (Ag) nanoparticles with a mean diameter of 10 nm with 99% of these Ag nanoparticles having a diameter within ±1 nm of that mean diameter, (iii) 30 ppm grape seed extract, and (iv) 20 ppm witch hazel. This stabilized multicomponent antimicrobial solution is readily applied to any dermal or other tissue region containing an infection or at risk of developing an infection, disease or condition.

Example 11

A stabilized multicomponent antimicrobial solution for dermal application is prepared and includes a 80% water 20% ethanol solution having (i) 3 ppm coral shaped gold (Au) nanoparticles with a mean length of 80 nm with 99% of these Au nanoparticles having a cross section within ±10 nm of that mean length and (ii) 5 ppm of spherical silver (Ag) nanoparticles with a mean diameter of 10 nm with 99% of these Ag nanoparticles having a diameter within ±1 nm of that mean diameter, and (iii) 20 ppm grape seed extract. This stabilized multicomponent antimicrobial solution is readily applied to any dermal or other tissue region containing an infection or at risk of developing an infection, disease or condition.

Example 12

A cream based carrier suitable for carrying a multicomponent antimicrobial composition is prepared by heating stearic acid, coconut oil, and emulsifying wax to between 160 and 200° F. Nanoparticles are suitably added after cooling the composition to about 105° F.

Example 13

A stabilized multicomponent antimicrobial solution for dermal application is prepared by adding to the cream carrier of Example 12 (i) 1 ppm coral shaped gold (Au) nanoparticles with a mean length of 80 nm with 99% of these Au nanoparticles having a length within ±10 nm of that mean cross section and (ii) 2 ppm of spherical silver (Ag) nanoparticles with a mean diameter of 15 nm with 99% of these Ag nanoparticles having a diameter within ±1.5 nm of that mean diameter and (iii) 10 ppm grape seed oil into which both the Ag and Au nanoparticles are added before the grape seed oil was added to the overall product. This stabilized multicomponent antimicrobial solution is readily applied to any dermal or other tissue region containing an infection or at risk of developing an infection, disease or condition.

Example 14

A stabilized multicomponent antimicrobial solution for dermal application is prepared by adding to the cream carrier of Example 12 (i) 3 ppm coral shaped gold (Au) nanoparticles with a mean length of 80 nm with 99% of these Au nanoparticles having a cross section within ±10 nm of that mean length and (ii) 5 ppm of spherical silver (Ag) nanoparticles with a mean diameter of 10 nm with 99% of these Ag nanoparticles having a diameter within ±1 nm of that mean diameter and (iii) 20 ppm grape seed oil into which both the Ag and Au nanoparticles were added before the grape seed oil is added to the overall product. This stabilized multicomponent antimicrobial solution is readily applied to any dermal or other tissue region containing a bacterial infection or at risk of developing an infection, disease or condition.

Example 15

A stabilized multicomponent antimicrobial solution for application to the face for the treatment and prevention of acne is prepared by heating stearic acid and emulsifying wax to between 160 and 200° F., then cooling to about 105° F. before adding (i) 0.5 ppm spherical gold (Au) nanoparticles with a mean diameter of 10 nm with 99% of these Au nanoparticles having a diameter within ±1 nm of that mean diameter, (ii) 1 ppm of spherical silver (Ag) nanoparticles with a mean diameter of 8 nm with 99% of these Ag nanoparticles having a diameter within ±1 nm of that mean diameter, (iii) 30 ppm arjuna bark extract, and (iv) a 2% concentration by weight of salicylic acid.

Example 16

A stabilized multicomponent antimicrobial solution for application to the face for the treatment and prevention of acne is prepared by heating stearic acid and emulsifying wax to between 160 and 200° F., then cooling to about 105° F. before adding (i) 1 ppm coral shaped gold (Au) nanoparticles with a mean length of 40 nm with 99% of these Au nanoparticles having a cross section within ±6 nm of that mean length, (ii) 2 ppm of spherical silver (Ag) nanoparticles with a mean diameter of 10 nm with 99% of these Ag nanoparticles having a diameter within ±1 nm of that mean diameter, (iii) 15 ppm grape seed extract, and (iv) a 2% concentration by weight of benzoyl peroxide.

Example 17

A stabilized multicomponent antimicrobial solution for administration by injection is prepared by adding to an isotonic sodium chloride solution (i) 0.5 ppm spherical gold (Au) nanoparticles with a mean diameter of 10 nm with 99% of these Au nanoparticles having a diameter within ±1 nm of that mean diameter, and (ii) 1 ppm of spherical silver (Ag) nanoparticles with a mean diameter of 8 nm with 99% of these Ag nanoparticles having a diameter within ±1 nm of that mean diameter. This stabilized multicomponent antimicrobial solution is readily administered by injection to treat MRSA or other tissue infection.

Example 18

A stabilized multicomponent antimicrobial solution for administration by injection is prepared by adding to a 0.45% w/v sodium chloride solution (i) 1 ppm coral shaped gold (Au) nanoparticles with a mean length of 40 nm with 99% of these Au nanoparticles having a cross section within ±6 nm of that mean length, (ii) 2 ppm of spherical silver (Ag) nanoparticles with a mean diameter of 10 nm with 99% of these Ag nanoparticles having a diameter within ±1 nm of that mean diameter, and (iii) 5% w/v dextrose. This stabilized multicomponent antimicrobial solution is readily administered by injection to treat MRSA or other tissue infection.

Example 19

A stabilized multicomponent antimicrobial solution for administration by injection is prepared by adding to a Riger's Lactate solution (i) 3 ppm coral shaped gold (Au) nanoparticles with a mean length of 80 nm with 99% of these Au nanoparticles having a cross section within ±10 nm of that mean length, and (ii) 5 ppm of spherical silver (Ag) nanoparticles with a mean diameter of 15 nm with 99% of these Ag nanoparticles having a diameter within ±1.5 nm of that mean diameter This stabilized multicomponent antimicrobial solution is readily administered by injection to treat MRSA or other tissue infection.

Example 20

A stabilized multicomponent antimicrobial solution for administration as a nasal spray is prepared by adding to an isotonic sodium chloride solution (i) 0.5 ppm spherical gold (Au) nanoparticles with a mean diameter of 10 nm with 99% of these Au nanoparticles having a diameter within ±1 nm of that mean diameter, (ii) 1 ppm of spherical silver (Ag) nanoparticles with a mean diameter of 8 nm with 99% of these Ag nanoparticles having a diameter within ±1 nm of that mean diameter, and (iii) benzyl alcohol at one micro molar concentration. This stabilized multicomponent antimicrobial solution is readily administered by inhalation to treat MRSA or other tissue infection.

Example 21

A stabilized multicomponent antimicrobial solution for administration by inhalation is prepared by adding to an isotonic sodium chloride solution (i) 1 ppm coral shaped gold (Au) nanoparticles with a mean length of 40 nm with 99% of these Au nanoparticles having a cross section within ±6 nm of that mean length, (ii) 2 ppm of spherical silver (Ag) nanoparticles with a mean diameter of 10 nm with 99% of these Ag nanoparticles having a diameter within ±1 nm of that mean diameter, and (iii) glycerin at one milli molar concentration. This stabilized multicomponent antimicrobial solution is readily administered by inhalation to treat MRSA or other tissue infection.

Example 22

A stabilized multicomponent antimicrobial emulsion for dermal application was prepared by adding to a stearic acid based cream, which also contains olive oil and emulsifying wax, (i) 3 ppm coral shaped gold (Au) nanoparticles with a mean length of 30 nm with 99% of these Au nanoparticles having a cross section within ±10 nm of that mean length, (ii) 3 ppm of spherical silver (Ag) nanoparticles with a mean diameter of 8 nm with 99% of these Ag nanoparticles having a diameter within ±1 nm of that mean diameter, (iii) 3 ppm of spherical Ag nanoparticles with a mean diameter of 15 nm with 99% of these Ag nanoparticles having a diameter within ±1.5 nm of that mean diameter, and (iv) 1 millimole of arjuna bark extract into which both the Ag and Au nanoparticles were added before the arjuna bark extract was added to the overall product. This stabilized multicomponent antimicrobial solution is readily applied to an infection, such as an area where methicillin resistant *Staphylococcus aureus* (MRSA) is present.

A female subject in the age range of 20-25 years, who had been diagnosed and treated 3 times for severe MRSA infections, was given the moisturizing cream as a carrier and stabilizing agent for the nanoparticles. As soon as she noticed the beginning of an infection (clearly defined by the level of pain produced by MRSA infections) the cream was applied 3-4 times per day. The infection disappeared within 2 days.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating a disease, condition, or infection on or in dermal tissue of a patient, comprising:
   applying a treatment composition to the dermal tissue of a patient in need thereof, the treatment composition comprising:
   a carrier,
   spherical nanoparticles that are made by laser ablation, are uncoated and nonionic with no external bond angles or edges, and have a mean diameter and particle size distribution such that at least 99% of the spherical nanoparticles have a diameter within 30% of the mean diameter and within ±3 nm of the mean diameter,
   coral-shaped metal nanoparticles each having a non-uniform cross section and a globular structure with multiple non-linear strands joined together without right angles, the coral-shaped nanoparticles consisting of particles that together provide a mean length and a size distribution where at least 99% of the particles have a length within 30% of the mean length,
   wherein the spherical nanoparticles and coral-shaped nanoparticles are each independently formed from at least one metal selected from the group consisting of gold, platinum, silver, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof; and
   the treatment composition treating the disease, condition, or infection on or in the dermal tissue of the patient without release of metal ions from the spherical nanoparticles and without toxicity to the patient.

2. The method of claim 1, wherein the disease, condition, or infection comprises a wound, cut, sore, ulcer, abrasion, or lesion.

3. The method of claim 1, further comprising the steps of:
   identifying a virus as a target microbe associated with the disease, condition, or infection on or in the dermal tissue of the patient; and
   selecting nanoparticles having a size that maximizes effectiveness in deactivating the virus, the selected nanoparticles having a particle size in a range of about 1 nm to about 7 nm.

4. The method of claim 1, further comprising the steps of:
identifying bacteria as a target microbe associated with the disease, condition, or infection on or in the dermal tissue of the patient; and
selecting nanoparticles having a size that maximizes effectiveness in killing the bacteria, the selected nanoparticles having a particle size in a range of about 7 nm to about 12 nm.

5. The method of claim 1, further comprising the steps of:
identifying a fungus as a target microbe associated with the disease, condition, or infection on or in the dermal tissue of the patient; and
selecting nanoparticles having a size that maximizes effectiveness in killing the fungus, the selected nanoparticles having a particle size in a range of about 12 nm to about 18 nm.

6. The method of claim 1, wherein the spherical nanoparticles comprise nonionic silver nanoparticles in which at least 99% of the silver nanoparticles have a diameter within 20% of the mean diameter and within ±2 nm of the mean diameter, wherein the nonionic silver nanoparticles have a ξ-potential with an absolute value of at least about 30 mV.

7. The method of claim 1, wherein the coral-shaped nanoparticles have a ξ-potential with an absolute value of at least about 30 mV such that the coral-shaped nanoparticles are resistant to agglomeration when dispersed in solution.

8. The method of claim 1, wherein the treatment composition further comprises a natural-based polyphenol.

9. The method of claim 1, wherein the carrier is a solvent carrier formed of one or more of water and alcohol.

10. The method of claim 1, wherein the disease, condition, or infection is located on or in the face of the patient, the method comprising applying the treatment composition to the face of the patient.

11. The method of claim 10, wherein the disease, condition, or infection includes acne and wherein the treatment composition treats the acne without releasing metal ions from the spherical nanoparticles.

12. The method of claim 1, wherein the disease, condition, or infection is located on or in the lips of the patient, the method comprising applying the treatment composition to the lips of the patient.

13. The method of claim 12, wherein the disease, condition, or infection includes herpes sores and wherein the treatment composition treats the herpes sores without releasing metal ions from the spherical nanoparticles.

14. The method of claim 1, wherein the disease, condition, or infection is located in dermal tissue infected with methicillin-resistant *Staphylococcus aureus* (MRSA) or that is at risk of becoming infected with MRSA.

15. The method of claim 14, wherein administering comprises applying the treatment composition onto or into a treatment area affected by a wound, sore, lesion, abscess, or surgical site, or to a treatment area as preparation for a surgical procedure, and the treatment composition killing or deactivating methicillin-resistant *Staphylococcus aureus* (MRSA) coming into contact with the treatment area without releasing metal ions from the spherical nanoparticles.

16. The method of claim 1, wherein the spherical nanoparticles are included at a concentration of about 0.5 ppm to about 100 ppm.

17. A method of treating a disease, condition, or infection on or in dermal tissue of a patient, comprising:
applying a treatment composition to the dermal tissue of a patient in need thereof, the treatment composition comprising:
a carrier,
spherical silver nanoparticles, wherein the spherical silver nanoparticles are made by laser ablation, are uncoated and nonionic with no external bond angles or edges, and have a mean diameter and particle size distribution such that at least 99% of the spherical silver nanoparticles have a diameter within 30% of the mean diameter and within ±3 nm of the mean diameter, and
coral-shaped gold nanoparticles each having a non-uniform cross section and a globular structure with multiple non-linear strands joined together without right angles, wherein the coral-shaped gold nanoparticles are made by laser ablation, are uncoated and nonionic, and wherein the coral-shaped nanoparticles consist of particles that together provide a mean particle size and particle size distribution such that at least 99% of the coral-shaped gold nanoparticles have a particle size within 30% of the mean particle size,
wherein the silver nanoparticles and the gold nanoparticles have a ξ-potential with an absolute value of at least about 30 mV; and
the treatment composition treating the disease, condition, or infection on or in the dermal tissue of the patient without release of silver ions from the silver nanoparticles, without release of gold ions from the gold nanoparticles, and without toxicity to the patient.

18. A method of treating a disease, condition, or infection on or in dermal tissue of a patient, comprising:
applying a treatment composition to the dermal tissue of a patient in need thereof, the treatment composition comprising:
a carrier,
spherical-shaped metal nanoparticles, and
coral-shaped metal nanoparticles each having a non-uniform cross section and a globular structure with multiple non-linear strands joined together without right angles, the coral-shaped nanoparticles consisting of particles that together provide a mean length with at least 99% of the particles having a length within 30% of the mean length,
the treatment composition treating the disease, condition, or infection on or in the dermal tissue of the patient.

19. The method of claim 18, wherein the mean length of the coral-shaped nanoparticles is in a range of about 15 nm to about 100 nm.

20. The method of claim 18, wherein the coral-shaped nanoparticles have a potential with an absolute value of at least about 30 mV such that the coral-shaped nanoparticles are resistant to agglomeration when dispersed in solution.

21. The method of claim 1, wherein the mean length of the coral-shaped nanoparticles is in a range of about 15 nm to about 100 nm.

* * * * *